United States Patent [19]

Furlenmeier et al.

[11] Patent Number: 4,816,582

[45] Date of Patent: Mar. 28, 1989

[54] ANTIMICROBIAL 2-OXO-1-AZETIDINESULPHONIC ACIDS

[75] Inventors: André Furlenmeier, Basel; Werner Hofheinz, Bottmingen, both of Switzerland; Christian N. Hubschwerlen, Durmenach, France; Hans P. Isenring, Sissach, Switzerland

[73] Assignee: Hoffmann-La Roche Inc., Nutley, N.J.

[21] Appl. No.: 111,480

[22] Filed: Oct. 22, 1987

Related U.S. Application Data

[60] Division of Ser. No. 835,395, Mar. 3, 1986, abandoned, which is a continuation of Ser. No. 499,971, Jun. 1, 1983, abandoned.

[30] Foreign Application Priority Data

Jun. 3, 1982 [CH] Switzerland ............... 3417/82
Apr. 29, 1983 [CH] Switzerland ............... 2320/83

[51] Int. Cl.$^4$ ............... C07D 417/12; C07D 401/14; C07D 417/14; C07D 403/14
[52] U.S. Cl. ............... 540/355; 546/209; 546/280; 548/170; 540/603
[58] Field of Search ............... 540/355

[56] References Cited

U.S. PATENT DOCUMENTS

4,572,801 2/1986 Matsuo ............... 540/355
4,576,751 3/1986 Hubschwerlen ............... 540/364
4,665,067 5/1987 Kishimoto ............... 540/355

FOREIGN PATENT DOCUMENTS

2071650 9/1981 United Kingdom .

Primary Examiner—Mark L. Berch
Attorney, Agent, or Firm—Jon S. Saxe; Bernard S. Leon; Richard J. Mazza

[57] ABSTRACT

Antimicrobial 2-oxo-1-azetidinesulphonic acids of the formula

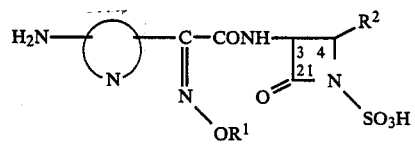

in which $H_2N$

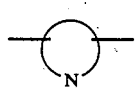

represents an amino-substituted thiazolyl group, $R^1$ is lower alkyl which is substituted by carbamoyl, lower alkylsuphonyl, azido, piperidine-carbonyl, (hexahydro-1H-azepin-1-yl)carbonyl or lower alkynyl, and $R^2$ is hydrogen or a lower organic group, typically, carbamoyloxymethyl.

6 Claims, No Drawings

ANTIMICROBIAL 2-OXO-1-AZETIDINESULPHONIC ACIDS

This is a division, of application Ser. No. 835,395 filed Mar. 3, 1986 now abandoned, which is a continuation of Ser. No. 499,971, filed June 1, 1983, abandoned.

The present invention is concerned with amides of the formula

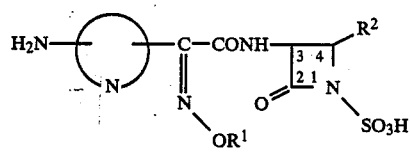   I in which the group

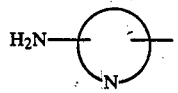

represents an amino-substituted, 5- or 6-membered, aromatic heterocycle containing 1 or 2 nitrogen atoms and optionally also an oxygen, selenium or sulphur atom, $R^1$ is lower alkyl which is substituted (a) by lower alkynyl, halogen, azido, amino, mono- or di-lower alkylamino, lower alkanoyloxyamino, lower alkanesulphonamido, benzenesulphonamido which is optionally substituted by amino, halogen, lower alkyl or lower alkoxy, tri-lower alkylammonio, thiocyanato, hydroxy, lower alkanoyloxy, carbamoyloxy, carbamoyl, di-lower alkylcarbamoyl, cyano, hydroxylaminocarbonyl, lower alkoxyaminocarbonyl, sulpho, sulphothio, phosphonato, mono- or di-lower alkylphosphonato, sulphamoyl, lower alkylthio, lower alkylsulphenyl or lower alkylsulphonyl or (b) by a 5- to 7-membered, aromatic, unsaturated or saturated heterocyclyl or heterocyclyl-CO- group which contains nitrogen and optionally also oxygen, selenium or sulphur and which is optionally substituted by lower alkyl, carbamoyl, sulpho-lower alkyl or mono- or di-lower alkylamino and $R^2$ is hydrogen or a lower organic group, the group $=NOR^1$ being present at least partially in the syn-form,
in racemic form or in the form of the 3S-enantiomer, and pharmaceutically compatible salts of these compounds.

The lower organic group denoted by $R^2$ can have diverse significances; for example, it can be lower alkyl, lower alkenyl, lower alkynyl, lower alkoxycarbonyl, lower alkoxycarbonyl-lower alkyl, lower alkoxycarbonyl-lower alkenyl, lower alkoxycarbonyl-lower alkynyl, lower alkanoyloxy-lower alkyl, hydroxyiminomethyl, lower alkoxyiminomethyl, carbamoyl, carbamoyl-vinyl or carbamoyloxy-lower alkyl.

The heterocycle

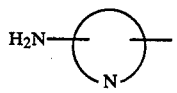

includes all 5- or 6-membered aromatic ring structures which contain 1 or 2 nitrogen atoms and which are substituted by an amino group; for example, aminopyridyl groups such as 2-amino-6-pyridyl and aminoimidazoyl groups such as 2-amino-4-imidazolyl. They can optionally contain an oxygen atom such as, for example, in the case of amino-oxazolyl groups, for example 2-amino-4-oxazolyl, or a sulphur atom such as, for example, in the case of amino-thiadiazolyl groups such as 5-amino-3-(1,2,4-thiadiazolyl) or, especially, in the case of amino-thiazolyl groups such as 2-amino-4-thiazolyl.

The term "lower alkyl" alone or in combinations signifies an aliphatic hydrocarbon group which can be straight-chain or branched-chain and which preferably contains up to 7 carbon atoms such as, for example, methyl, ethyl, n-propyl, isopropyl, n-butyl, isobutyl, sec-butyl, t-butyl, n-pentyl, isopentyl, n-hexyl, n-heptyl etc. The term "lower alkoxy" alone or in combinations has an analogous significance. The term "lower alkenyl" signifies an olefinic hydrocarbon group which can be straight-chain or branched-chain and which preferably contains up to 7 carbon atoms such as, for example, vinyl, allyl, isopropenyl, 2-methallyl, 2-butenyl, 3-butenyl, 2-hexenyl, 2-heptenyl etc. The term "lower alkynyl" signifies an acetylenic hydrocarbon group which can be straight-chain or branched-chain and which preferably contains up to 7 carbon atoms such as, for example, ethynyl, 1-propynyl, 2-propynyl, 2-hexynyl, 2-heptynyl etc. The term "lower alkanoyloxy" alone or in combinations signifies an aliphatic carboxylic acid residue which preferably contains up to 7 carbon atoms such as, for example, acetoxy, propionyloxy and isobutyryloxy. The term "halogen" means all 4 halogens, especially chlorine and bromine. The heterocyclyl group referred to in the definition of formula I can be, for example, imidazolyl, pyrrolyl, pyridinio, morpholinyl, thiamorpholinyl, 1H-5-tetrazolyl, 1H-1-methyl-5-tetrazolyl, 1H-1-(2-dimethylaminoethyl)-5-tetrazolyl, piperidinyl or hexahydro-1H-azepin-1-yl.

Preferred groups denoted by $R^1$ are:

—CH$_2$—C≡CH
—CH$_2$—CH$_2$—Hal
—CH$_2$—CH$_2$—SO$_2$CH$_3$
—CH$_2$—CH$_2$—NH$_2$
—CH$_2$—CH$_2$—N(CH$_3$)$_2$
—CH$_2$—CH$_2$—N$^+$(CH$_3$)$_3$

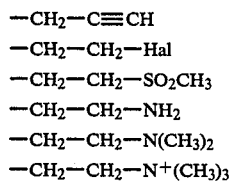

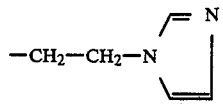

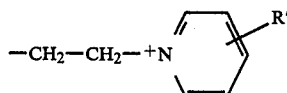

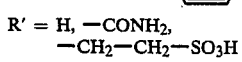

—CH$_2$—CH$_2$—SCN
—CH$_2$—CN
—CH$_2$—CONR'R''
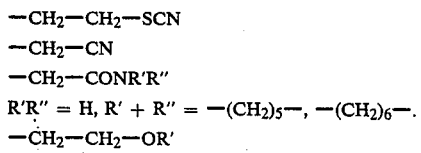
—CH$_2$—CH$_2$—OR'

-continued

R' = H, —COCH₃, —CONH₂
—CH₂—CO—NHOH
—CH₂—SO₃H
—CH₂—SO₂NH₂

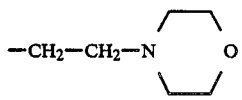

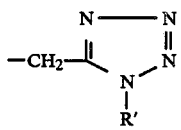

R' = H, —CH₃, —CH₂CH₂N(CH₃)₂

—CH₂CH₂—NH—SO₂—CH₃

Preferred groups denoted by R² are methyl, ethyl, n-propyl, vinyl, allyl, ethynyl, 3-(acetoxy)-n-propyl, methoxycarbonyl, hydroxyiminomethyl, methoxyiminomethyl, carbamoyl and carbamoyloxymethyl.

The compounds of formula I can be present in various isomeric forms [e.g. cis, trans; syn (Z-form), anti (E-form); and as the 3S-enantiomer]. This also applies to the starting materials of formulae II-V hereinafter. Thus, for example, the thioesters of formula IIa hereinafter can be present as syn- or anti-forms. The syn-form or mixtures in which the syn-form predominates are preferred.

The products of formula I can be present as free acids or as betains or also as pharmaceutically compatible salts which are obtained by salt formation with a basic salt former on a free carboxy or sulpho group. Examples of basic salt formers are, for example, inorganic cations such as sodium and potassium ions, basic amino acids such as arginine, ornithine, lysine or histidine, polyhydroxyalkylamines such as N-methylglucamine, diethanolamine, triethanolamine etc. Basic groups such as the amino group in the substituent in the 3-position can form acid addition salts with acidic salt formers. Examples of such acidic salt formers are organic acids such as acetic acid, tartaric acid, ethanesulphonic acid etc, inorganic acids such as hydrochloric acid, hydrobromic acid, sulphuric acid and phosphoric acid, and acidic amino acids such as arginine, aspartic acid, glutamic acid etc.

Examples of amides of formula I which can be manufactured in accordance with the present invention are the products described in Examples 1-19 hereinafter not only in the form in which they are present in the Examples (3S-enantiomer or racemate), but also in the form of pharmaceutically compatible salts of these compounds.

The amides of formula I and their pharmaceutically compatible salts are manufactured in accordance with the invention by
(a) reacting a carboxylic acid of the formula

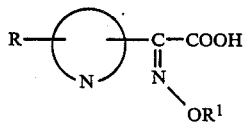

II in which
R¹ is as above and

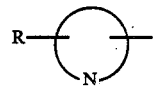

is the same as

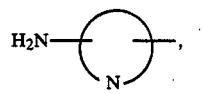

whereby, however,
R is optionally protected amino, and the group =NOR¹ is present at least partially in the syn-form, or a functional derivative thereof with a compound of the formula which is present in racemic form or in the form of the 3-S-enantiomer

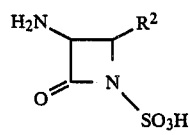

III in which R² is as above,
or with a salt thereof and subsequently cleaving off an amino protecting group which may be present, or
(b) sulphonating a compound of the formula which is present in racemic form or in the form of the 3S-enantiomer

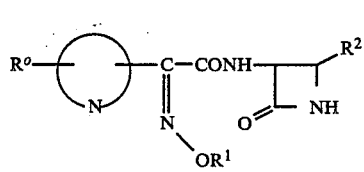

IV in which
R¹ and R² are as above and

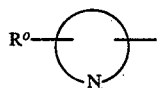

is the same as

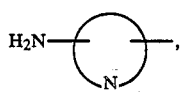

whereby, however, R⁰ is protected amino, and the group =NOR¹ is present at least partially in the syn-form,
or a salt thereof and subsequently cleaving off the amino protecting group, or
(c) for the manufacture of a compound of formula I in which R² is hydroxyiminomethyl, lower alkoxyiminomethyl or carbamoyl-vinyl, reacting a compound of the formula which is present in racemic form or in the form of the 3S-enantiomer

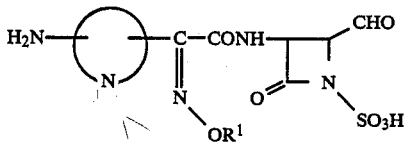

in which $R^1$ and

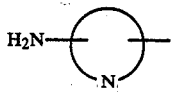

are as above and the group $=NOR^1$ is present at least partially in the syn-form,
with hydroxylamine, with an O-lower-alkylhydroxylamine or with carbamoylmethylenetriphenylphosphorane and, if desired, lower alkylating a product obtained in which $R^2$ is hydroxyiminomethyl, or (d) for the manufacture of a compound of formula I in which R is a group $R^{13}$, which is lower alkyl which is substituted by a 5- to 7-membered aromatic, unsaturated or saturated heterocyclyl group which contains nitrogen and optionally also oxygen, selenium or sulphur and which is optionally substituted by lower alkyl, carbamoyl, sulpho-lower alkyl or mono- or di-lower alkylamino, reacting a compound of the formula which is present in racemic form or in the form of the 3S-enantiomer

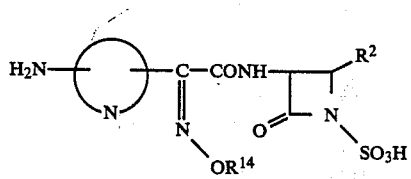

in which $R^2$ and

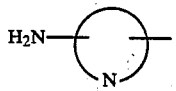

are as above and $R^{14}$ is iodo-lower alkyl or bromo-lower alkyl,
with a compound of the formula

HR¹³ wherein
$R^{13}$ is as above,
or
(e) for the manufacture of a compound of formula I in which $R^1$ is a group of $R^{15}$, which is lower alkyl which is substituted by azido or lower alkylsulphonyl, reacting a compound of formula Ia with a compound of the formula

MR¹⁵ wherein
$R^{15}$ is as above and M is an alkali metal cation,
or
(f) for the manufacture of a compound of formula I in which $R^1$ is amino-lower alkyl, catalytically hydrogenating a compound of formula I in which $R^1$ is azido-lower alkyl, or
(g) converting a compound of formula I into a pharmaceutically compatible salt.

The reaction in accordance with the invention of a carboxylic acid of formula II or a functional derivative thereof with a compound of formula III can be carried out in a manner known per se. Where the free carboxylic acid of formula II is used, the reaction is preferably carried out in the presence of a condensation agent which can be, for example, a substituted carbodiimide such as N,N-dicyclohexylcarbodiimide, a quaternary 2-halopyridinium salt (e.g. 2-chloro-1-methyl-pyridinium iodide) or 1-chloro-N,N,2-trimethyl-1-propenamine. As functional derivatives of the carboxylic acids of formula II there come into consideration acid halides (e.g. acid chlorides), acid anhydrides (e.g. mixed anhydrides with $C_{1-7}$-alkanecarboxylic acids such as acetic acid), active amides (e.g. amides with pyrazole, imidazole or benztriazole), active esters (e.g. $C_{1-7}$-alkyl, methoxymethyl, 2-propynyl, 4-nitrophenyl or hydroxysuccinimide esters) or active thioesters (e.g. esters with 2-pyridinethiol or 2-benzthiazolylthiol). The last-mentioned thioesters, i.e. the 2-benzthiazolyl thioesters, are particularly preferred for the manufacture of amides of formula I in which $R^1$ is lower alkyl which is substituted (a) by lower alkynyl, di-lower alkylamino, lower alkanoyloxyamino, lower alkanesulphonamido, benzenesulphonamido which is optionally substituted by amino, halogen, lower alkyl or lower alkoxy, thiocyanato, hydroxy, lower alkanoyloxy, carbamoyloxy, carbamoyl, cyano, lower alkoxyaminocarbonyl, di-lower alkylphosphonato, sulphamoyl, lower alkylthio, lower alkylsulphenyl or lower alkylsulphonyl or (b) by a 5- to 7-membered, aromatic, unsaturated or saturated heterocyclyl or heterocyclyl-CO- group which contains nitrogen and optionally also oxygen, selenium or sulphur and which is optionally substituted by lower alkyl, carbamoyl or di-lower alkylamino. The reaction of a compound of formula II or a functional derivative thereof with a compound of formula II which is carried out according to variant (a) of the process in accordance with the invention is conveniently carried out in an inert organic solvent, for example in a chlorinated hydrocarbon such as methylene chloride or chloroform, in an ether such as tetrahydrofuran or dioxan, in an ester such as ethyl acetate, in a ketone such as acetone, in an aprotic solvent such as acetonitrile, dimethylformamide or dimethylacetamide or in a mixture of one of these solvents with water. The reaction is conveniently carried out at a temperature between about −40° C. and +60° C., advantageously between −15° C. and +25° C., especially between 0° C. and 20° C. The reaction is conveniently carried out using about stoichiometric amounts of the reactants or using a slight excess of the carboxylic acid of formula II or of a functional derivative thereof. The reaction is advantageously carried out in the presence of a base such as, for example, in the presence of an organic amine such as triethylamine or N-methylmorpholine or in the presence of an alkali metal bicarbonate such as sodium bicarbonate.

The group R in the starting material of formula II or a functional derivative thereof preferably represents the unprotected amino group (since thereby one reaction step, the subsequent cleavage of the amino protecting group, can be dispensed with). However, R can also represent a protected amino group. The amino protecting group can be a conventional amino protecting amino group; for example, a protecting group which is cleavable by acid hydrolysis such as t-butoxycarbonyl, benzhydryl, trityl or formyl, a protecting group which is cleavable by basic hydrolysis such as trifluoroacetyl or a chloroacetyl, bromoacetyl or iodoacetyl group which can be cleaved off using thiourea. The amino group can also be protected by salt formation with a mineral acid (e.g. hydrochloric acid). After the reaction of a carboxylic acid of formula II with a compound of formula III or of a functional derivative of a carboxylic acid of formula II with a compound of formula III, an amino protecting group which may be present is cleaved off. Protecting groups which are cleavable by acid hydrolysis are preferably removed with the aid of a mineral acid or a lower alkanecarboxylic acid which, if desired, can be halogenated. In particular, there is used hydrochloric acid, formic acid or trifluoroacetic acid (the latter optionally in the presence of anisole) or also pyridinium hydrochloride. This cleavage is usually carried at room temperature, although it can also be carried out at a slightly higher or slightly lower temperature (e.g. a temperature in the range of about 0° C. to +40° C.). Protecting groups which are cleavable using alkali are generally hydrolyzed with dilute aqueous caustic alkali at 0° C. to 30° C. The chloroacetyl, bromoacetyl and iodoacetyl protecting groups can be cleaved off using thiourea in an acidic, neutral or alkaline medium at about 0° C. to 30° C.

In accordance with variant (b) of the process in accordance with the invention, a compound of formula IV is sulphonated. This sulphonation can be carried out in a manner known per se by reaction with sulphur trioxide or a reactive derivative thereof, for example complexes of sulphur trioxide with an organic base such as pyridine, dimethylformamide, picoline etc. The reaction is carried out, for example, at about −10° C. to 80° C. in an inert organic solvent, for example in an ether such as dioxan, in an ester such as ethyl acetate, in a chlorinated hydrocarbon such as methylene chloride or in acetonitrile, dimethylformamide or pyridine.

In variant (b) of the process in accordance with the invention, the amino group of the residue

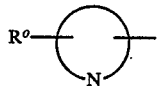

is protected. The amino protecting groups are of the same kind as the amino protecting groups in the starting materials of formula II and they can also be cleaved off in the same manner as described earlier.

The aldehydes of formula V used as starting materials in variant (c) of the process in accordance with the invention can be prepared in the manner described above from a carboxylic acid of formula II or a functional derivative thereof and a compound of formula III in which $R^2$ represents the 2,2-dimethyl-1,3-dioxolan-4-yl group

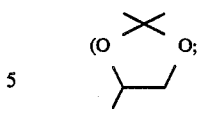

see formula 17 in Scheme III hereinafter). In the resulting product of formula I this group $R^2$ can be converted by treatment with a lower alkanol such as methanol or in an aqueous ether such as aqueous dioxan or tetrahydrofuran in the presence of an acidic catalyst such as a sulphonated ion exchanger, p-toluenesulphonic acid, dilute mineral acid and the like, preferably at room temperature to about 60° C., into the corresponding diol ($R^2$=—CHOH—CH$_2$OH) and the diol group can be converted into the formyl group by treatment with aqueous alkali metal metaperiodate (e.g. sodium metaperiodate) at about room temperature.

The reaction of an aldehyde of formula V with hydroxylamine according to variant (c) of the process in accordance with the invention yields a compound of formula I in which $R^2$ is hydroxyiminomethyl. This reaction is preferably carried out in an inert organic solvent (e.g. methylene chloride), preferably in the presence of an organic base such as pyridine. The reaction is advantageously carried out at about 0°–60° C., especially at about room temperature. If an O-lower-alkylhydroxylamine is used in place of hydroxylamine, there is obtained a compound of formula I in which $R^2$ is lower alkoxyiminomethyl.

If desired, a thus-obtained compound of formula I in which $R^2$ is hydroxyiminomethyl can be lower alkylated. This lower alkylation is preferably carried out using a $C_{1-7}$-alkyl iodide, advantageously in an inert organic solvent such as acetonitrile, tetrahydrofuran, ethanol or dimethylformamide, preferably in the presence of an organic base such as pyridine. The lower alkylation is preferably carried out at a temperature of about 0° C. to 60° C., especially at about room temperature.

If the starting material of formula V is reacted with carbamoylmethylenetriphenylphosphorane, there is obtained a compound of formula I in which $R^2$ is carbamoyl-vinyl. This reaction is preferably carried out in an inert solvent such as methylene chloride, tetrahydrofuran or dioxan and at a temperature between about room temperature and the boiling point of the mixture.

The reactiion of a compound of formula Ia with a compound of the formula HR$^{13}$ in accordance with variant (d) of the process in accordance with the invention is preferably carried out in an inert organic, preferably polar, solvent such as acetonitrile, dimethylformamide or acetone at about room temperature to 100° C. The compound of the formula HR$^{13}$ can itself also serve as the solvent, for example when it is pyridine.

The reaction of a compound of formula Ia with a compound of the formula HR$^{15}$ in accordance with variant (e) of the process in accordance with the invention can be carried out in the same manner. The compound MR$^{15}$ is preferably used as the sodium salt, for example sodium methylsulphinate or sodium azide.

Variant (f) of the process in accordance with the invention, i.e. the catalytic hydrogenation of the azide group to amino, is preferably carried out using a noble metal catalyst such as palladium/carbon and a lower alkanol such as methanol or ethanol, conveniently at a temperature between about room temperature and about b 80° C.

The manufacture of the salts of the compounds of formula I in accordance with variant (g) of the process in accordance with the invention can be carried out in a manner known per se; for example, by reacting an acid of formula I with an equivalent amount of the desired base or by reacting a base of formula I with an equivalent amount of the desired acid. In both cases, the reaction is conveniently carried out in a solvent such as water or an organic solvent such as ethanol, methanol, acetone and the like. The temperature at which the salt formation is carried out is not critical, but it generally lies in the range of about 0° C. to 50° C., preferably at room temperature.

The acid starting materials of formula II can be prepared, for example, by reacting an ester of the formula

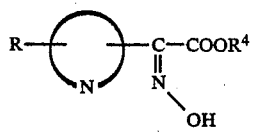     VI in which the group

is as above and COOR⁴ is an esterified carboxy group, especially one in which $R^4$ is lower alkyl, phenyl-lower alkyl or phenyl, and the group =NOH is present at least partially in the syn-form, with a halide of the formula Hal—R¹     VII wherein $R^1$ is as above
and Hal is halogen.

Conveniently, a chloride or bromide of formula VII is reacted with a methyl, ethyl, benzyl or benzhydryl ester of formula VI in an inert organic solvent such as acetonitrile or dimethylformamide at about room temperature. It is advantageous to carry out the reaction in the presence of a base such as an alkali metal carbonate, triethylamine or N-ethyldiisopropylamine and in the presence of an alkali metal iodide such as sodium iodide.

A resulting ester of the formula

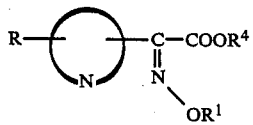     VIII wherein

$R^1$ and $R^4$ are as above and the group =NOR¹ is present at least partially in the syn-form, is subsequently saponified; for example, by reacting a lower alkyl ester with caustic alkali in a lower alkanol such as methanol or by catalytically hydrogenating (e.g. with palladium/carbon) a benzyl or benzhydryl ester. A liberated carboxylic acid of formula II can subsequently be converted into one of its functional derivatives; into an acid halide by reaction with a thionyl halide (e.g. thionyl chloride), into an acid anhydride by reaction with an alkanecarboxylic acid, into an active amide by reaction with e.g. carbonyldiimidazole, into an active ester by reaction with a corresponding alcohol. The preferred 2-benzthiazolyl thioesters of the formula

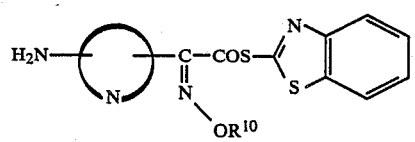     IIa in which

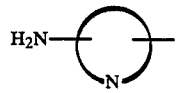

is as above and $R^{10}$ is lower alkyl which is substituted (a) by lower alkynyl, di-lower alkylamino, lower alkanoyloxyamino, lower alkansulphonamido, benzenesulphonamido which is optionally substituted by amino, halogen, lower alkyl or lower alkoxy, thiocyanato, hydroxy, lower alkanoyloxy, carbamoyloxy, carbamoyl, cyano, lower alkoxyaminocarbonyl, di-lower alkylphosphonato, sulphamoyl, lower alkylthio, lower alkylsulphenyl or lower alkylsulphonyl or (b) by a 5- to 7-membered, aromatic, unsaturated or saturated hetercyclyl or heterocyclyl-CO- group which contains nitrogen and optionally also oxygen, selenium or sulphur and which is optionally substituted by lower alkyl, carbamoyl or di-lower alkylamino, and the group =NOR¹⁰ is present at least partially in the syn-form, can be prepared in an advantageous manner by reacting a carboxylic acid of the formula

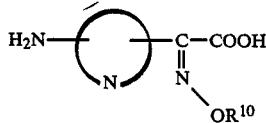     IIb in which

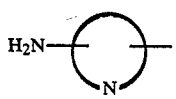

and $R^{10}$ are as above and the group =NOR¹⁰ is present at least partially in the syn-form, with dithio-bis-benzthiazole in the presence of a tri-(lower alkyl)-phosphite and a base or in the presence of triphenylphosphine.

The temperature at which the last-mentioned reaction is carried out conveniently lies between about −30° C. and +50° C., advantageously between about −20° C. and +25° C. The reaction is advantageously carried out in an organic solvent, for example in acetonitrile or in methylene chloride. The preferred embodiment comprises carrying out the reaction in the presence of a tri-(lower alkyl)-phosphite and a base. Triethyl phosphite is preferably used as the tri-(lower alkyl)-phosphite and an organic base, especially a tertiary organic base such as treithylamine, N-ethyldiisopropylamine or, preferably, N-methylmorpholine, is preferably used as the base.

A particular problem arises in the preparation of the carboxylic acid starting materials of formula II in which $R^1$ represents cyano-lower-alkyl. The conventional manner for the preparation of such carboxylic acids, namely the reaction of the methyl or ethyl ester of the corresponding hydroxyimino compound with a halo-lower-alkyl nitrile and subsequent saponification does not yield the desired carboxylic acid of formula II in which $R^1$ represents cyano-lower-alkyl, because the cyano group is thereby transformed into carbamoyl. It is therefore necessary to adopt a different procedure.

The aforementioned carboxylic acids of formula II in which $R^1$ is cyano-lower-alkyl can, however, be prepared in good yield when in place of the aforementioned methyl or ethyl ester there is used the allyl, t-alkyl (especially t-butyl), trityl or methylsulphonylethyl ester, i.e. by cleaving off the group $R^{40}$ in an ester of the formula

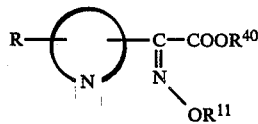

VIIIa in which

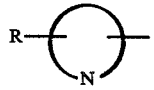

is as above, $R^{11}$ is cyano-lower-alkyl and $R^{40}$ is allyl, methylsulphonylethyl or the group —$C(R^5)_3$ in which $R^5$ is $C_{1-3}$-alkyl or phenyl, the group $=NOR^{11}$ being present at least partially in the syn-form.

The term "$C_{1-3}$-alkyl" is methyl, ethyl, n-propyl and isopropyl.

According to one embodiment of the above process, an ester of formula VIIIa in which $R^{40}$ is allyl is cleaved catalytically. This cleavage can be carried out by the action of a palladium compound in the presence of triphenylphosphine or a tri-(lower alkyl)-phosphite (e.g. triethyl phosphite). As palladium compounds these come into consideration palladium/carbon and palladium salts, especially salts with hydrohalic acids such as hydrochloric acid or hydrobromic acid or with lower alkanecarboxylic acids such as acetic acid or propionic acid. Palladium-organic complexes with triphenylphosphine or a tri-(lower alkyl)-phosphite such as triethyl phosphite also come into consideration, whereby the reaction can also be carried out without the additional triphenylphosphine or tri-(lower alkyl)-phosphite. A further reaction partner is an alkali lower-alkanoate, for example sodium acetate or, preferably, sodium-2-ethyl-caproate, or, alternatively, an organic base such as N-methylmorpholine or triethylamine. The reactiion can be carried out at a temperature between about 0° C. and 100° C., but preferably at room temperature (when palladium/carbon is used the reaction is preferably carried out at a somewhat higher temperature; about 50°–80° C.). The reaction is preferably carried out in an inert organic solvent (e.g. in ethyl acetate or methylene chloride).

According to a further embodiments of the above process, an ester of formula VIIIa in which $R^{40}$ is the group —$C(R^5)_3$ is cleaved acidolytically, for example by treatment with trifluoroacetic acid. The reaction can be carried out in the presence or absence of a solvent; when a solvent is used this is an inert organic solvent (e.g. methylene chloride or anisole). The reaction is preferably carried out at a temperature in the range of about −10° C. to +15° C.

According to a further embodiment of the above process, an ester of formula VIIIa in which $R^{40}$ is the methylsulphonylethyl group is cleaved. This cleavage is preferably carried out by treatment with aqueous concentrated alkali carbonate solution (e.g. potassium carbonate) at a pH of about 10 to 10.5. This cleavage is preferably carried out at a temperature in the range of about room temperature to 60° C., especially at 30° C. to 35° C.

The ally esters of formula VIIIa above can be prepared starting from diketene, chlorine gas and allyl alcohol, which is converted into allyl 4-chloroacetoacetate. The latter is nitrosated with nitrous acid and subsequently converted with thiourea into the allyl 2-(2-amino-4-thiazolyl)-2-(Z)-hydroxyimino-acetate which is thereupon converted into the allyl ester of formula VIIIa with a halo-lower-alkane nitrile (e.g. chloroacetonitrile or bromoacetonitrile) in the presence of a base such as an alkali carbonate, triethylamine or N-ethyldiisopropylamine.

Esters of formula VIIIa in which $R^{40}$ is the group —$C(R^5)_3$ (e.g. t-butyl) can be prepared in a manner analogous to that described above for the preparation of the allyl esters of formula VIIIa by replacing allyl alcohol by an alcohol of the formula $C(R^5)_3OH$ (e.g. t-butanol). When an ester in which $R^{40}$ is methylsulphonylethyl is required, 2-(methylsulphonyl)-ethanol is used as the alcohol.

The starting materials of formula III can be obtained according to various methods. For the preparation of optically uniform compounds of formula III having the 3S-cis configuration, one can start from isopropylidene-L-glyceraldehyde in accordance with the following Formulae Schemes (Schemes I-VII). The preparation of optically uniform compounds of formula II having the 3S-trans configuration is illustrated in Schemes V and VI:

Scheme I

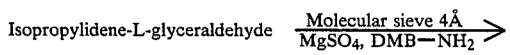

13
-continued
Scheme I
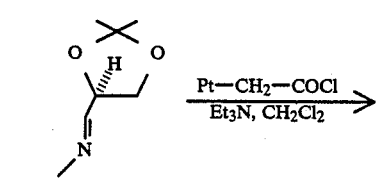
1
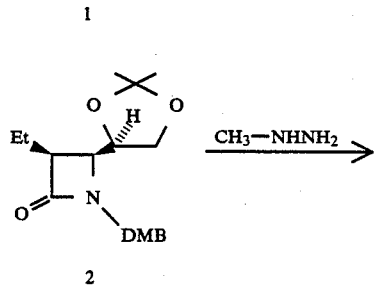
2
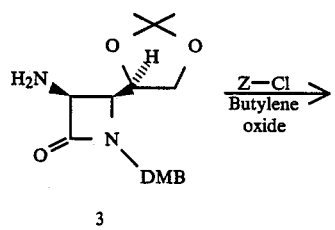
3
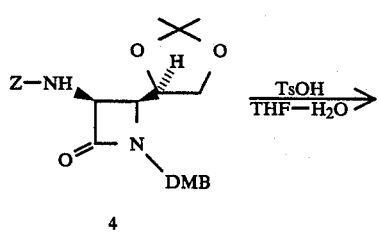
4
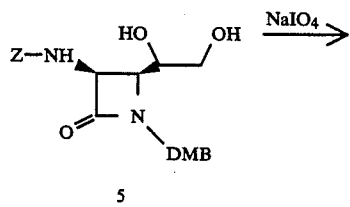
5
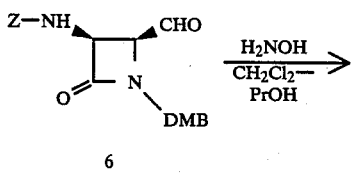
6
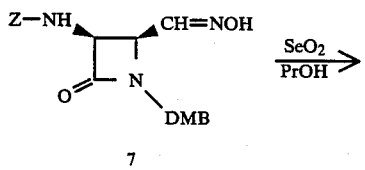
7
14
-continued
Scheme I
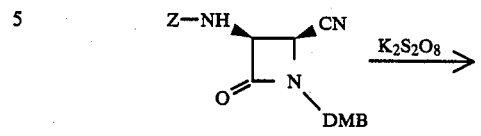
8
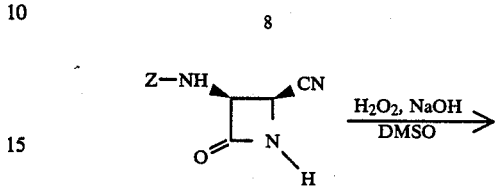
9
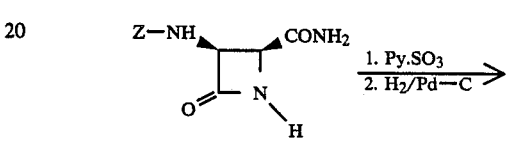
10
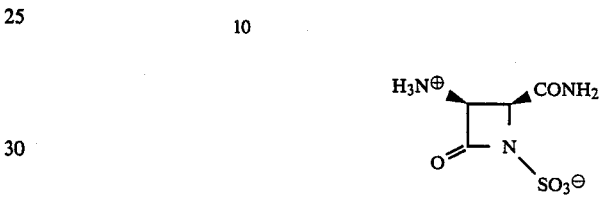
11
Scheme II
6
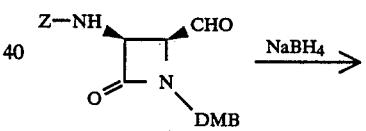
12
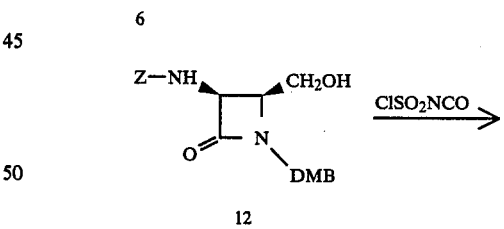
13
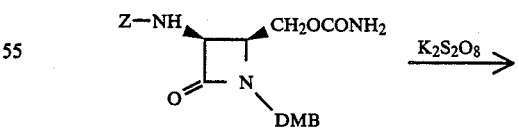
14

Scheme II -continued
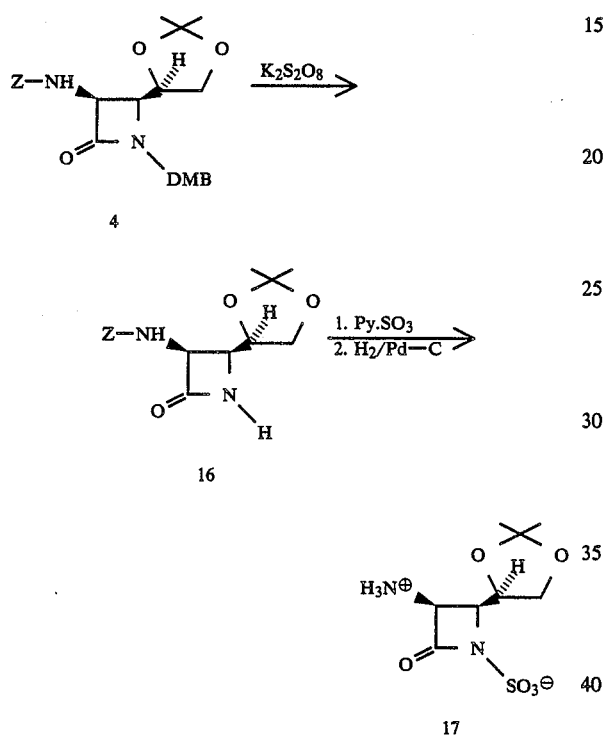
Scheme III
Scheme IV
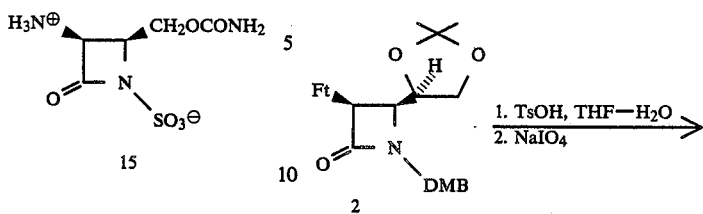
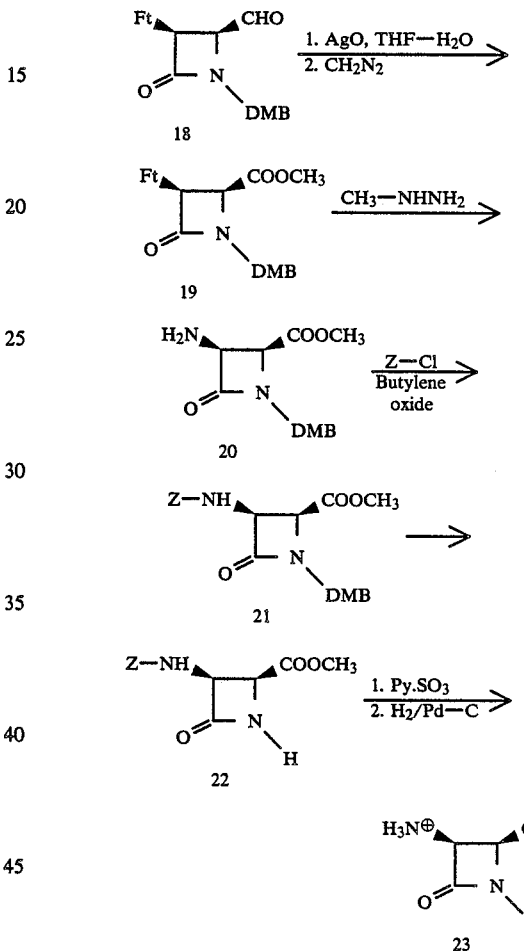
Scheme V
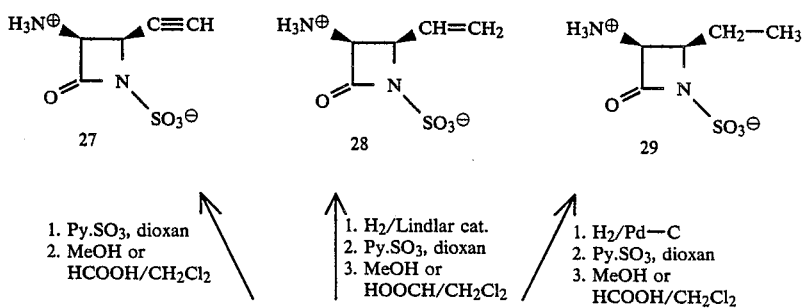

Scheme V
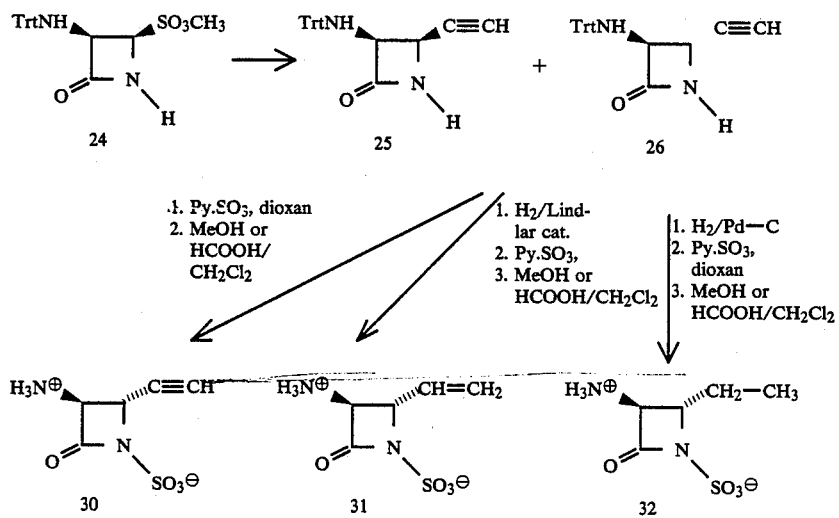

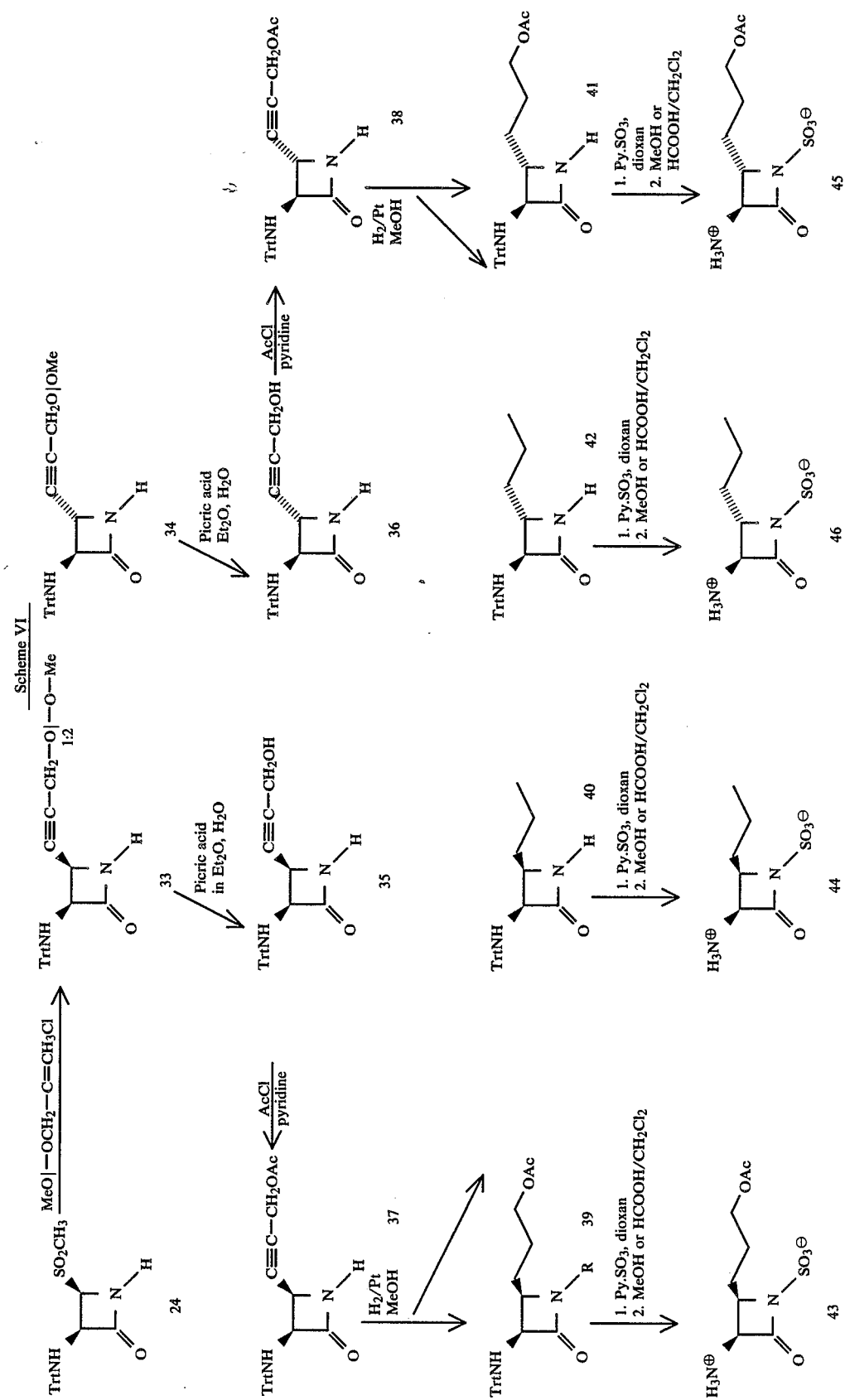

Scheme VII

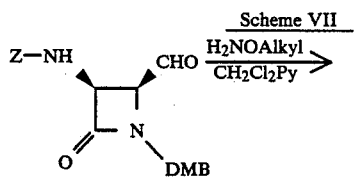

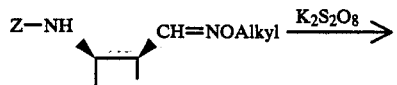

trum of activity, especially against gram-negative microorganisms such as, for example, pathogens of the family Enterobacteriaceae, for example *Escherichia coli*, *Proteus* spp., *Serratia* spp. and *Pseudomonas aeruginosa*.

These products can accordingly be used for the treatment and prophylaxis of infectious diseases. A daily dosage of about 10–600 mg/kg body weight comes into consideration for adults.

The minimum inhibitory concentration (MIC, μg/ml) in vitro of some representative products is given in Table 1 hereinafter in which specific compounds obtained in the Examples hereinafter are referred to.

TABLE 1

| Organism | Example 1 | Example 2 | Example 4 | Example 5 | Example 6 | Example 9 | Example 10 | Example 11 |
|---|---|---|---|---|---|---|---|---|
| E. cloacae 15 M | ≦0.1 | 0.25 | 0.5 | 0.5 | 0.12 | 8 | 4 | 8 |
| S. marcescens 80315 | 0.2 | 0.25 | 1 | 0.5 | 0.12 | 4 | 4 | 4 |
| Pr. mirabilis 2117 | ≦0.1 | ≦0.06 | 0.12 | 0.03 | ≦0.03 | 0.5 | 1 | 1 |
| Pr. vulgaris 1028 | ≦0.1 | 0.12 | 0.25 | 0.06 | 0.06 | 2 | 8 | 4 |
| Ps. aeruginosa 799/61 | ≦0.1 | ≦0.12 | 0.25 | 0.06 | ≦0.03 | 2 | 2 | 2 |
| E. coli 1346 | ≦0.1 | ≦0.06 | 0.06 | ≦0.03 | ≦0.03 | 0.06 | 0.25 | 0.12 |
| K. pneumoniae 418 | ≦0.1 | 0.12 | 0.25 | 0.25 | 0.06 | 2 | 0.5 | 2 |
| E. oxytoca 22812 | ≦0.1 | 0.5 | 2 | 0.5 | 0.5 | 2 | 4 | 4 |
| Organism | Example 12 | Example 13 | Example 14 | Example 15 | Example 16 | Example 17 | Example 18 | Example 19 |
| E. cloacae 15 M | 4 | 2 | 1 | 0.25 | 16 | 32 | 4 | 16 |
| S. marcescens 80315 | 4 | 2 | 1 | 0.25 | 16 | 16 | 4 | 16 |
| Pr. mirabilis 2117 | 1 | 0.12 | 0.5 | 0.06 | 8 | 8 | 1 | 8 |
| Pr. vulgaris 1028 | 4 | 0.25 | 1 | 0.06 | 8 | 16 | 1 | 4 |
| Ps. aeruginosa 799/61 | 2 | 0.25 | 0.25 | 0.12 | 16 | 32 | 8 | 8 |
| E. coli 1346 | 0.12 | ≦0.03 | 0.25 | ≦0.03 | 0.12 | 0.25 | 0.12 | 0.12 |
| K. pneumoniae 418 | 2 | 1 | 0.5 | 0.5 | 8 | 16 | 4 | 8 |
| K. oxytoca 22812 | 2 | 1 | 1 | 1 | 8 | 16 | 8 | 8 |

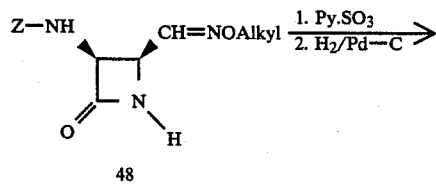

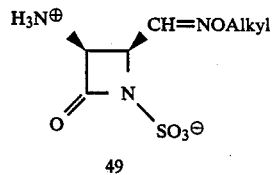

ABBREVIATIONS USED IN SCHEMES I-VII

DMB=2,4-dimethoxybenzyl
Ft=phthalimido
Et=ethyl
Me=methyl
TSOH=p-toluenesulphonic acid
THF=tetrahydrofuran
PrOH=n-propanol
DMSO=dimethyl sulphoxide
Py=pyridine
Py.SO$_3$=sulphur trioxide-pyridine complex
Z=benzyloxycarbonyl
Trt=trityl
Ac=lower alkanoyl (e.g. acetyl).

The compounds of formula I and their pharmaceutically compatible salts have a broad antimicrobial spec- The products provided by the present invention can be used as medicaments; for example, in the form of pharmaceutical preparations which contain them in admixture with a pharmaceutical, organic or inorganic inert carrier material which is suitable for enteral or parenteral administration.

The following Examples illustrate the present invention:

EXAMPLE 1

(a) 224 mg (1 mmol) of rac,cis-3-amino-4-methoxycarbonyl-2-oxo-1-azetidinesulphonic acid, 433 mg (1.1 mmol) of 2-(2-amino-4-thiazolyl)-2-(Z)-(carbamoylmethoxyimino)-acetic acid 2-benzthiazolyl thioester and 202 mg of triethylamine are stirred at room temperature in 5 ml of dichloromethane for 26 hours. The insoluble material is filtered off and taken up in 50 ml of water. After filtration the solution is lyophilized. There are obtained 312 mg of rac,cis-3-[(Z)-2-(2-amino-4-thiazolyl)-2-[(carbamoylmethoxy)imino]acetamido]-4-(methoxycarbonyl-2-oxo-1-azetidinesulphonic acid triethylamine salt as an amorphous lyophilizate.

Elemental analysis for $C_{18}H_{29}N_7O_9S_2$ (551.59): Calculated: C 39.20, H, 5.30, N 17.78%. Found: C 39.25, H 5.19, N 17.67%.

IR (KBr, cm$^{-1}$): 3327, 3197, 1780, 1676, 1626, 1536, 1278, 1246, 1047.

NMR (DMSO, ppm): 9.61 (d, J=8.5 Hz, 1H), 7.48 (s, br., 1H), 7.27 (s, br., 2H), 7.10 (s, br., 1H), 6.67 (s, 3H), 5.43 (dd, J=5.5/8.5 Hz, 1H), 4.50 (d, J=5.5 Hz, 1H), 4.38 (s, br., 2H), 3.59 (s, 3H), 3.11 (q, J=7.1 Hz, 6H), 1.18 (q, J=7.1 Hz, 9H).

The 2-(2-amino-4-thiazolyl)-2-(Z)-(carbamoylmethoxyimino)-acetic acid 2-benzthiazolyl thioester used as the starting material can be prepared as follows:

(b) 54 g of ethyl 2-(2-amino-4-thiazolyl)-2-(Z)-hydroxyimino-acetate are suspended in 1 l of acetonitrile and the suspension is treated gradually with 46.7 g of 2-chloroacetamide, 129 ml of N-ethyldiisopropylamine and 75 g of sodium iodide. The suspension is stirred at room temperature for 12 hours. 3 l of water are subsequently added thereto, the mixture is extracted with 7 l of ethyl acetate and the extract is washed three times with 1.5 l of water. After drying over magnesium sulphate and subsequent concentration to a small volume, the crystallized-out product is filtered off under suction. Yield: 34.3 g; melting point 182° C.

(c) 47.9 g of ethyl 2-(2-amino-4-thiazolyl)-2-(Z)-(carbamoylmethoxyimino)-acetate are dissolved in 3.6 l of methanol and 240 ml of water and the solution is treated with 176 ml of 1N sodium hydroxide solution. The clear solution is stored at room temperature for 48 hours. 1 l of water is subsequently added and the methanol is removed in vacuo. The aqueous solution is washed twice with ethyl acetate and treated with 176 ml of 1N hydrochloric acid. The precipitated acid is filtered off under suction and dried. Yield: 34.9 g; melting point 179° C.

(d) 6.2 g of 2-(2-amino-4-thiazolyl)-2-(Z)-(carbamoylmethoxyimino)-acetic acid are suspended in 300 ml of acetonitrile together with 3.3 ml of N-methylmorpholine and 8 g of 2,2-dithio-bis-benzthiazole. A solution of 6 ml of triethyl phosphate in 40 ml of acetonitrile is added dropwise at room temperature while stirring within 3 hours. The mixture is subsequently stirred for a further 30 minutes. The thioester formed is filtered off under suction and dried. Yield: 5.8 g; melting point 151°–152° C.

EXAMPLE 2

(a) 250 mg (1.19 mmol) of (3S,4S)-3-amino-4-carbamoyl-2-oxo-1-azetidinesulphonic acid are dispersed in 3 ml of dimethylformamide and treated with 470 ml (1.19 mmol) of 2-(2-amino-4-thiazolyl)-2-(Z)-(carbamoylmethoxyimino)-acetic acid 2-benzothiazolyl thioester and 100 mg (1.20 mmol) of sodium bicarbonate. The mixture is stirred at room temperature for 3 days, subsequently diluted with water and filtered. The mother liquor obtained is chromatographed on MCI gel using water as the eluting agent. There are obtained 325 mg (59.5%) of (3,4S)-3-[(Z)-2-(2-amino-4-thiazolyl)-2-[(carbamoylmethoxy)imino]acetamido]-4-carbamoyl-2-oxo-1-azetidinesulphonic acid.

Elemental analysis for $C_{11}H_{12}N_7O_8S_2Na$: Calculated: C 28.89, H 2.64, N 21.44%. Found: C 30.08, H 3.06, N 21.30%.

IR (KBr, cm$^{-1}$): 3282, 1790, 1640, 1612, 1527, 1260.

NMR (DMSO, ppm): 3.85, (3H, s, OCH$_3$), 4.3 (1H, d, 6 Hz, CH—CONH$_2$), 5.30 (1H, dd, 6 and 9 Hz, NH—CH), 6.95 (1H, s, S—CH=), 7.40 (2H, d, 18 Hz, CONH$_2$), 9.25 (1H, d, 9 Hz, NH—CO).

The (3S,4S)-3-amino-4-carbamoyl-2-oxo-1-azetidinesulphonic acid used as the starting material can be prepared as follows:

(b) 17 g (42.7 mmol) of benzyl (3S,4S)-cis-1-(2,4-dimethoxybenzyl)-4-formyl-2-oxo-3-azetidinecarbamate are dissolved in 100 ml of methylene chloride and 100 ml of n-propanol. This solution is treated with 3.5 g (50.3 mmol) of hydroxylamine hydrochloride, followed by 4.2 ml (52 mmol) of pyridine. The mixture is heated under reflux for 2 hours. The methylene chloride is subsequently removed by distillation and a solution of 6.3 g (57 mmol) of selenium dioxide in 100 ml of n-propanol is added dropwise. The mixture is heated under reflux for 2 hours, cooled to room temperature and filtered. The solution obtained is evaporated under reduce pressure. The oil obtained is dissolved in 100 ml of n-propanol and the solution is evaporated. This procedure is repeated twice. The partially crystalline residue obtained is taken up in 250 ml of methylene chloride and washed successively twice with two 200 ml portions of water and two 200 ml portions of sodium chloride solution. After drying over sodium sulphate, filtration and evaporation of the solvent, the residue is taken up in 70 ml of n-propanol. The solution is left to stand in a refrigerator for 12 hours. There are obtained 16.4 g (97%) of benzyl (3S,4S)-cis-1-(2,4-dimethoxybenzyl)-4-cyano-2-oxo-3-azetidinecarbamate of melting point 152°–153° C.; $[\alpha]_D = +10.6°$ (c=1 in chloroform).

MS: 395 (M+).

(c) 15.72 g (58.2 mmol) of potassium peroxydisulphate and 9.5 g (54.8 mmol) of potassium hydrogen sulphate are dissolved in 480 ml of water. The solution is heated to 80° C. and treated with a solution of 1.2 g of copper sulphate in 10 ml of water. The suspension obtained is diluted with 180 ml of acetonitrile and treated dropwise with a solution of 14.4 g of benzyl (3S,4S)-cis-1-(2,4-dimethoxybenzyl)-4-cyano-2-oxo-3-azetidinecarbamate in 300 ml of acetonitrile. The mixture is heated under reflux for 2.5 hours, subsequently cooled, filtered and partially evaporated. The oily aqueous solution obtained is extracted with ethyl acetate and the organic phase is washed successively three times with saturated aqueous sodium bicarbonate solution, water and sodium chloride solution. After drying and evaporation of the solvent, the oil obtained is chromatographed on silica gel [230–400 mesh, eluting agent: ethyl acetate/n-hexane (1:1)]. There are obtained 6.1 g (68.3%) of benzyl (3S,4S)-cis-4-cyano-2-oxo-3-azetidinecarbamate of melting point 163°–165° C.

MS: 245 (M+).

(d) 6.16 g (25 mmol) of benzyl (3S,4S)-cis-4-cyano-2-oxo-3-azetidinecarbamate are dissolved in 45 ml of dimethyl sulphoxide and the solution is treated with 5.58 ml of 30% aqueous hydrogen peroxide. After the temperature has returned to 25° C., the mixture is treated with 5 ml of aqueous 1N sodium hydroxide solution. The temperature rises to 55° C. A precipitate results after stirring for 45 minutes. 20 ml of ethyl acetate are added thereto and the crystals obtained are filtered off. The crystals are washed with aqueous ethanol and absolute ether. There are obtained 2.48 g (37.5%) of benzyl (3S,4S)-4-carbamoyl-2-oxo-3-azetidinecarbamate of melting point 248°–249° C.; $[\alpha]_D = +13°$ (c=1 in dimethyl sulphoxide).

The mother liquor is partially evaporated, a further 0.33 g of product being isolated. The thus-obtained mother liquor is diluted with water and chromatographed on MCI gel using ethanol/water (3:7) for the elution. The total yield of product amounts to 3.0 g (45.4%).

(e) 7.9 g (30 mmol) of benzyl (3S,4S)-4-carbamoyl-2-oxo-3-azetidinecarbamate are dispersed in 470 ml of absolute dioxan and treated with 6.2 g (39 mmol) of pyridine-sulphur trioxide complex. The suspension obtained is stirred at room temperature for 2 hours, subsequently treated with 1.41 g (8.8 mmol) of pyridine-sulphur trioxide complex and stirred for a further hour. After the addition of 1.90 g (12 mmol) of pyridine-sulphur trioxide complex and stirring for a further 2 hours, the solvent is removed by evaporation under reduced pressure and the residue is taken up in 200 ml of water. The aqueous solution obtained is treated with 15 g (44.24 mmol) of tetrabutylammonium hydrogen sulphate and extracted twice with 250 ml of methylene chloride each time. After drying over sodium sulphate and evaporation of the solvent, the oily residue obtained is dissolved in 150 ml of absolute methanol and the solution is hydrogenated for 2 hours over 2.5 g of 10% palladium/carbon. The catalyst is filtered off, the solution is evaporated and the residue is taken up in a solution of 70 ml of formic acid in 100 ml of methylene chloride. After 2 hours, the solvent is removed by evaporation and the residue is treated with 25 ml of water. 2.3 g (36%) of (3S,4S)-3-amino-4-carbamoyl-2-oxo-1-azetidinesulphonic acid are obtained in the form of colourless crystals. The mother liquor is chromatographed on MCI gel using water/ethanol (1:0 to 9:1) for the elution, a further 420 mg of product being obtained. The total yield is 2.7 g (43.3%).

IR (KBr, cm$^{-1}$): 1779, 1696, 1633, 1485, 1288, 1250.

NMR (d$_6$-DMSO, ppm): 4.43 and 4.72 (2×1H, 2d, 6 Hz, CH—CH), 7.88 (2H, d, br., NH$_2$), 8.59 (3H, br., NH$_3$+).

EXAMPLE 3

(a) 150 mg (957 mmol) of (3S,4S)-3-amino-4-carbamoyloxymethyl-2-oxo-1-azetidinesulphonic acid sodium salt are dissolved in 6 ml of water/acetone (1:1) and the solution is treated at room temperature with 248 mg (0.63 mmol) of 2-(2-amino-4-thiazolyl)-2-[(Z)-(carbamoylmethoxyimino)-acetic acid 2-benzthiazolyl thioester. The mixture is stirred for 3 days and subsequently diluted with 40 ml of acetone. The suspension is filtered. The crystals obtained are dispersed in water and filtered. The solution obtained is subjected to reverse-phase chromatography using water as the eluting agent. 170 mg (61%) of (3S,4S)-3-[(Z)-2-(2-amino-4-thiazolyl)-2-[(carbamoylmethoxy)imino]acetamido]-4-carbamoyloxymethyl-2-oxo-1-azetidinesulphonic acid sodium salt are obtained.

Elemental analysis for C$_{11}$H$_{13}$N$_6$O$_8$S$_2$Na: Calculated: C 29.73, H 2.95, N 18.91%. Found: C 29.91, H 3.30, N 19.00%.

IR (KBr, cm$^{-1}$): 3364, 1775, 1730, 1680, 1625, 1537, 1284, 1256.

NMR (DMSO, ppm): 3.90 (3H, s, OCH$_3$), 4.10 (3H, m, CH—CH$_2$), 5.25 (1H, dd, 4.5 and 9 Hz, CH—NH), 6.45 (2H, s, NH$_2$), 6.70 (1H, s, S—CH=), 7.10 (2H, s, NH$_2$), 9.10 (1H, d, 9 Hz, CONH).

The (3S,4S)-3-amino-4-carbamoyloxymethyl-2-oxo-1-azetidinesulphonic acid sodium salt used as the starting material can be prepared as follows:

(b) To a solution, stirred at room temperature, of 0.9 g (5.4 mmol) of 2,4-dimethoxybenzylamine in 100 ml of methylene chloride are added 3 g of molecular sieve 4 Å and, after 20 minutes, 0.7 g (5.4 mmol) of isopropylidene-L-glyceraldehyde and 5 g of anhydrous magnesium sulphate. The mixture is subsequently stirred at room temperature for a further 1 hour. The organic solution of isopropylidene-L-glyceraldehyde (2,4-dimethoxybenzyl)imine obtained is cooled to −20° C. under argon and treated while stirring with 0.88 ml (5.4 mmol) of triethylamine. A solution of 1.25 g (5.6 mmol) of phthaloylglycyl chloride in 20 ml of dry methylene chloride is then added dropwise within 1 hour and subsequently the mixture is stirred at room temperature overnight. The mixture is washed three times with 100 ml of water each time and with 100 ml of sodium chloride solution and then dried over sodium sulphate. After evaporation, the residue is chromatographed on silica gel (230–400 mesh) while eluting with n-hexane/ethyl acetate (1:1). There are obtained 1.77 g (70%) of N-[(3S,4S)-cis-1-(2,5-dimethoxybenzyl)-4-[(R)-2,2-dimethyl-1,3-dioxolan-4-yl]-2-oxo-3-azetidinyl]phthalimide in the form of a foam; [α]$_D$= +41° (c=0.8 in chloroform); MS: 466 (M+).

(c) A solution of 149.3 g (0.32 mol) of N-[(3S,4S)-cis-1-(2,4-dimethoxybenzyl)-4-[(R)-2,2-dimethyl-1,3-dioxolan-4-yl]-2-oxo-3-azetidinyl]phthalimide in 2.5 l of methylene chloride is treated with 34 ml (0.64 mol) of methylhydrazine. The mixture is stirred at 28° C. overnight, precipitated material is filtered off and the filtrate is evaporated under reduced pressure. The residue is taken up in 1.2 l of ethyl acetate and the suspension obtained is filtered. The filtrate is washed three times with 500 ml of water each time and with 500 ml of sodium chloride solution and then dried over sodium sulphate. After evaporation of the solvent, there are obtained 104.3 g (86.8%) of crude (3S,4S)-cis-3-amino-1-(2,4-dimethoxybenzyl)-4-[(R)-2,2-dimethyl-1,3-dioxolan-4-yl]-2-azetidinone which is used in the next step without further purification.

(d) A stirred solution of 104 g (0.31 mol) of (3S,4S)-cis-3-amino-1-(2,4-dimethoxybenzyl)-4-[(R)-2,2-dimethyl-1,3-dioxolan-4-yl]-2-azetidinone and 104 ml (1.2 mol) of butylene oxide in 1.5 l of methylene chloride is treated with 57.6 ml (0.4 mol) of carbobenzoxy chloride, the mixture is stirred for 1 hour and subsequently evaporated under reduced pressure. The crude material obtained is crystallized in 2 l of dry ether. There are obtained 122.6 g (84%) of benzyl (3S,4S)-cis-1-(2,4-dimethoxybenzyl)-4-[(R)-2,2-dimethyl-1,3-dioxolan-4-yl]-3-oxo-3-azetidinecarbamate of melting point 115°–116° C.; [α]$_D$= +48° (c=0.3 in methanol).

(e) A stirred solution of 7 g (15.0 mmol) of benzyl (3S,4S)-cis-1-(2,4-dimethoxybenzyl)-4-[(R)-2,2-dimethyl-1,3-dioxolan-4-yl]-2-oxo-2-azetidinecarbamate in 250 ml of acetonitrile is treated dropwise at 90° C. and under argon with a solution of 16.2 g (60 mmol) of potassium peroxydisulphate and 10.5 g (60 mmol) of potassium hydrogen sulphate in 420 ml of water. After the addition, the mixture is stirred for 2 hours, left to cool and the pH is adjusted to 6–7 by the addition of excess potassium hydrogen sulphate (about 6 g). The mixture is filtered and the filtrate is evaporated under reduced pressure. The residue is taken up in 250 ml of methylene chloride, washed four times with 80 ml of water each time and with 80 ml of sodium chloride solution. After drying and evaporation, the oily residue is chromatographed on a silica gel column (particle size: 230°–400 mesh) while eluting with ethyl acetate/n-hexane (7:3). There are obtained 2.5 g (52%) of benzyl (3S,4S)-cis-4-[(R)-2,2-dimethyl-1,3-dioxolan-4-yl]-2-oxo-3-azetidinecarbamate of melting point 142° C.; [α]= +57° (c=0.5 in methanol).

(f) A solution of 160 g (0.34 mol) of benzyl (3S,4S)-cis-4-[(R)-2,2-dimethyl-1,3-dioxolan-4-yl]-2-oxo-3-azetidinecarbamate in 1000 ml of tetrahydrofuran and 400 ml of water is stirred at 60° C. overnight in the presence of 8 g of p-toluenesulphonic acid. The mixture is neutralized with saturated sodium bicarbonate solution and the tetrahydrofuran is removed by evaporation. The aqueous solution is then extracted with 2 l of ethyl acetate. After drying over sodium sulphate and evaporation, there are obtained 142 g (97.2%) of pure benzyl (3S,4S)-cis-4-[(R)-1,2-dihydroxyethyl]-1-(2,4- dimethoxybenzyl)-2-oxo-3-azetidinecarbamate of melting point 177°–178° C. (from methanol).

(g) A solution of 142 g (0.33 mol) of benzyl (3S,4S)-cis-4-[(R)-1,2-dihydroxyethyl]-1-(2,4-dimethoxybenzyl)-2-oxo-3-azetidinecarbamate in 1000 ml of tetrahydrofuran is treated dropwise while stirring with a solution of 76.8 g (0.359 mol) of sodium metaperiodate in 600 ml of water. The mixture is stirred for 1 hour, filtered and the filtrate is evaporated under reduced pressure. The residue is taken up in 400 ml of ethyl acetate and washed twice with 100 ml of water each time and with 50 ml of sodium chloride solution. After drying and evaporation, there are obtained 105 g (87.8%) of pure benzyl (3S,4S)-cis-1-(2,4-dimethoxybenzyl)-4-formyl-2-oxo-3-azetidinecarbamate of melting point 145°–147° C. (from ethyl acetate/hexane); $[\alpha]_D = +13.7°$ (c=1 in chloroform).

(h) 4.27 g (113 mmol) of sodium borohydride are dissolved in 1.6 l of absolute ethanol. The solution, cooled to 0° C., is treated dropwise with a solution of 90 g (226 mmol) of benzyl (3S,4S)-cis-1-(2,4-dimethoxybenzyl)-4-formyl-2-oxo-3-azetidinecarbamate in 720 ml of ethanol/tetrahydrofuran (1:1). The mixture is stirred at 0° C. for 2 hours, subsequently treated with 350 ml of saturated aqueous sodium sulphate solution and then stirred for 45 minutes. After filtration and evaporation of the solvent, the residue is taken up in 1.5 l of ethyl acetate and washed until neutral. After drying over sodium sulphate and partial evaporation, there are obtained 72.2 g (79.6%) of crystalline (3S,4S)-cis-benzyloxycarboxamido-1-(2,4-dimethoxybenzyl)-4-hydroxymethyl-2-azetidinone in the form of colourless crystals of melting point 138° C.; $[\alpha]_D = +41.6°$ (c=1 in methanol).

Elemental analysis for $C_{21}H_{24}N_2O_6$: Calculated: C 62.99, H 6.04, N 7.00%. Found: C 62.76, H 6.09, N 6.96%.

IR (KBr, cm$^{-1}$): 1718, 1698, 1615, 1589.

NMR (CDCl$_3$, ppm): 2.45 (1H, dd, OH), 3.55–3.75 (3H, br., CH—CH$_2$—), 3.79 (6H, s, 2×OCH$_3$), 4.35 (2H, 2, N—CH$_2$), 5.08 (2H, s, $\phi$—CH$_2$), 5.02–5.11 (1H, dd, 5 and 9 Hz, H$_3$), 6.06 (1H, d, 9 Hz, NH), 6.43 (2H, m, Ar), 7.15 (1H, m, Ar), 7.31 (5H, m, C$_6$H$_5$).

MS: 292 (M—BzOH).

(i) A solution of 30 g (74.9 mmol) of (3S,4S)-cis-3-benzyloxycarboxamido-1-(2,4-dimethoxybenzyl)-4-hydroxymethyl-2-azetidinone in 600 ml of methylene chloride is treated at 0°–5° C. with 21.22 g (2 equivalents) of chlorosulphonyl-isocyanate. After 15 minutes, the mixture is added dropwise to an aqueous solution, cooled to 5° C., of 20.9 g (2.7 equivalents) of sodium sulphite. The mixture is stirred for 2 hours, subsequently diluted with methylene chloride, the organic phase is separated, washed with aqueous sodium chloride solution and dried over sodium sulphate for 12 hours. The organic phase is subsequently treated with magnesium sulphate and stirred for a further 2 hours. After filtration and evaporation of the solvent, the residue is treated with ether. The crystals obtained are filtered off and washed with ether. There are obtained 32.6 g (97%) of (3S,4S)-cis-3-benzyloxycarboxamido-4-carbamoyloxymethyl-1-(2,4-dimethoxybenzyl)-2-azetidinone of melting point 178°–179° C.; $[\alpha]_D = +84.7°$ (c=0.8 in chloroform).

Elemental analysis for $C_{22}H_{25}N_3O_7$: Calculated: C 59.59, H 5.68, N 9.48%. Found: C 59.17, H 5.69, N 9.37%.

IR (KBr, cm$^{-1}$): 1761, 1708, 1618, 1587.

(k) A suspension of 11.9 g (26.8 mmol) of (3S,4S)-cis-3-benzyloxycarboxamido-4-carbamoyloxymethyl-1-(2,4-dimethoxybenzyl)-2-azetidinone, 14.5 g (53.5 mmol) of potassium peroxydisulphate, 13.98 g (80.3 mmol) of dipotassium hydrogen phosphate and 1.33 g (5.36 mmol) of copper sulphate pentahydrate in 270 ml of acetonitrile and 130 ml of water is heated to 95° C. under an argon atmosphere for 3.5 hours at a pH between 6.5 and 7.0 (occasional addition of 10 g of dipotassium hydrogen sulphate). After cooling and filtration, the aqueous phase is discarded and the organic phase is evaporated. The residue is taken up in ethyl acetate and washed with water and sodium chloride solution. After drying over sodium sulphate, filtration and evaporation of the solvent, the residue is taken up in ether and filtered. The crude crystals (8.9 g) are chromatographed on SiO$_2$ [300 g, 40–63 µm, chloroform/methanol/ethyl acetate (85:10:5)]. There are obtained 5.5 g (70%) of (3S,4S)-cis-3-benzyloxycarboxamido-4-carbamoyloxymethyl-2-azetidinone in the form of colourless crystals; $[\alpha]_D = +61.2+$ (c=1 in methanol); melting point 193°–195° C.

Elemental analysis for $C_{13}H_{15}N_3O_5$: Calculated: C 53.24, H 5.16, N 14.33%. Found: C 53.40, H 5.24, N 14.35%.

IR (KBr, cm$^{-1}$): 3414, 3315, 1757, 1701, 1610, 1540, 1498.

NMR (d$_6$-DMSO, ppm): 3.31–4.06 (3H, m, CH—CH$_2$), 4.95 (1H, dd, 4.5 and 9 Hz, H$_3$), 5.06 (2H, s, $\phi$—CH$_2$), 6.53 (2H, br, NH$_2$), 7.35 (5H, s, C$_6$H$_5$), 7.95 (1H, d, 9 Hz, CH$_3$—NH—CO), 8.35 (1H, s, NH—CO).

MS (CI with NH$_3$): 251 (M+H)$^+$—CONH=

(1) 5.4 g (18.4 mmol) of (3S,4S)-cis-3-benzyloxycarboxamido-4-carbamoyloxymethyl-2-azetidinone in 200 ml of absolute dioxan are treated at room temperature with 4.3 g (1.3 equivalents) of pyridine-sulphur trioxide complex. The suspension obtained is stirred for 3 hours, subsequently treated with a further 0.99 g (0.3 equivalents) of pyridine-sulphur trioxide complex and the mixture is stirred for a further hour. After the addition of a further 1.37 g (0.4 equivalents) of pyridine-sulphur trioxide complex and stirring for a further 2 hours, the solvent is partially removed under reduced pressure and the residue is treated with 110 ml of saturated aqueous sodium bicarbonate solution. The brown solution obtained is left to stand in a refrigerator for 12 hours. The crystals obtained are filtered off. The mother liquor is chromatographed on MCI gel using water/ethanol (1:1 to 9:1) for the elution. After lyophilization, there are obtained 3.5 g (49%) of (3S,4S)-cis-3-benzyloxycarboxamido-4-carbamoyloxymethyl-2-azetidinone-1-sulphonic acid sodium salt in the form of a colourless powder; $[\alpha]_D = +29.6°$ (c=0.5 in water).

Elemental analysis for $C_{13}H_{14}N_3O_8SNa$: Calculated: C 39.50, H 3.57, N 10.63%. Found: C 39.41, H 3.45, N 10.36%.

IR (KBr, cm$^{-1}$): 1798, 1758, 1739, 1693, 1584, 1547.

NMR (d$_6$-DMSO, ppm): 3.9–4.4 (3H, CH—CH$_2$), 4.9 (dd, 1H, NH—CH), 5.1 (s, 2H, $\phi$—CH$_2$), 6.4 (2H, br., NH$_2$), 7.4 (5H, s, C$_6$H$_5$), 8.0 (1H, d, NH).

(m) 3.065 g (7.73 mmol) of (3R,4S)-cis-benzyloxycarboxamido-4-carbamoyloxymethyl-2-azetidinone-1-sulphonic acid sodium salt are dissolved in 180 ml of absolute methanol and the solution is hydrogenated for 1 hour in the presence of 1.5 g of 10% palladium/carbon. The catalyst is removed by filtration and the solution obtained is evaporated. 2.02 g (100%) of (3S,4S)-cis-3- amino-4-carbamoyloxymethyl-2-oxo-1-azetidinesulphonic acid sodium salt are obtained.

IR (KBr, cm$^{-1}$): 3444, 3207, 1754, 1725, 1611, 1249.

EXAMPLE 4

(a) 340 mg (0.89 mmol) of (3S,4S)-3-benzyloxyformamido-4-[(methoxyimino)methyl]-2-oxo-1-azetidinesulphonic acid sodium salt (E/Z mixture) are dissolved in 30 ml of absolute methanol and the solution is hydrogenated in the presence of 10% palladium/carbon. The catalyst is filtered off and the solvent is removed by evaporation. The residue is dissolved in 60 ml of acetone/water (1:1) and the solution is stirred at room temperature for 2 days with 388 mg (0.98 mmol) of 2-(2-amino-4-thiazolyl)-2-(Z)-(carbamoylmethoxyimino)-acetic acid 2-benzthiazolyl thioester. The acetone is removed by evaporation under reduced pressure. The crystals remaining are filtered off. The mother liquor is chromatographed on MCI gel using water as the eluting agent. There are obtained 57 mg (14%) of (3S,4S)-3-[(Z)-2-(2-amino-4-thiazolyl)-2-(carbamoylmethoxy)-imino]acetamido]-4-[(E/Z)-(methoxyimino)methyl]-2-oxo-1-azetidinesulphonic acid sodium salt.

Elemental analysis for $C_{12}H_{14}N_7O_8S_2$: Calculated: C 30.58, H 2.99, N 20.80%. Found: C 31.60, H 3.60, N 20.94%.

IR (KBr, cm$^{-1}$): 3432, 3334, 1772, 1677, 1622, 1533, 1275.

The (3S,4S)-3-benzyloxyformamido-4-[(methoxyimino)methyl]-2-oxo-1-azetidinesulphonic acid sodium salt (E/Z mixture) used as the starting material can be prepared as follows:

(b) 3.0 g (7.5 mmol) of benzyl (3S,4S)-[1-(2,4-dimethoxyphenyl)-4-formyl-2-oxo-3-azetidinyl]carbamate are dissolved in 40 ml of methylene chloride and the solution is treated with 0.7 g (8.5 mmol) of O-methylhydroxylamine hydrochloride and 0.73 ml (9.0 mmol) of pyridine. The mixture is stirred at room temperature for 2 days and subsequently washed with water and sodium chloride solution. After drying over sodium sulphate and evaporation of the solvent, the material is chromatographed on silica gel [230–400 mesh, ethyl acetate/n-hexane (6:4)]. There are obtained 2.6 g (82%) of benzyl (3S,4S)-1-(2,4-dimethoxybenzyl)-4[(methoxyimino)methyl]-2-oxo-3-azetidinecarbamate (E/Z mixture).

IR (KBr, cm$^{-1}$): 3290, 1772, 1636, 1210.
MS: 319

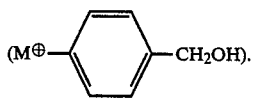

(c) 11.9 g (44 mmol) of potassium peroxydisulphate and 9.6 g of dipotassium hydrogen phosphate are dispersed in 110 ml of acetonitrile and 350 ml of water. The mixture is heated to 78° C. and a solution of 11.8 g (27.6 mmol) of benzyl (3S,4S)-1-(2,4-dimethoxybenzyl)-4-[(methoxyimino)methyl]-2-oxo-3-azetidinecarbamate (E/Z mixture) in 300 ml of acetonitrile is added dropwise thereto. The pH of the solution is held at 7 by the addition of dipotassium hydrogen phosphate. After boiling for 6 hours, the mixture is cooled, the aqueous phase is discarded, the organic phase is diluted with 65 ml ethyl acetate and washed successively with water, aqueous sodium bicarbonate solution and sodium chloride solution. After drying over sodium sulphate, the solvent is removed by evaporation and the crude mixture is chromatographed [230–400 mesh, ethyl acetate/n-hexane (8:2)], there being obtained 1.7 g (27%) of benzyl (3S,4S)-4-[(methoxyimino)methyl]-2-oxo-3-azetidinecarbamate (E/Z mixture); melting point 170°–171° C.

IR (KBr, cm$^{-1}$): 3310, 3210, 1790, 1732, 1533, 1258.

(d) 1.7 g (6.13 mmol) of benzyl (3S,4S)-4-[(methoxyimino)methyl]-2-oxo-3-azetidinecarbamate (E/Z mixture) are dissolved in 100 ml of absolute dioxan, the solution is treated with 1.26 g (7.9 mmol) of sulphur trioxide-pyridine complex and the mixture is stirred at room temperature for 1.5 hours. After the addition of a further 0.29 g (1.8 mmol) of sulphur trioxide-pyridine complex, the suspension is stirred for a further 1.5 hours. After the addition of 0.39 g (2.45 mmol) of sulphur trioxide-pyridine complex and stirring for a further 1 hour, the solvent is removed by evaporation under reduced pressure and the residue is treated with 30 ml of saturated aqueous sodium bicarbonate solution. The aqueous solution obtained is extracted twice with ethyl acetate and the organic phase is discarded. The aqueous phase is evaporated to 10 ml and chromatographed on MCI gel using water/ethanol (1:0 to 9:1 to 7:3) for the elution. There are obtained 1.36 g (58.5%) of (3S,4S)-3-(benzyloxyformamdio)-4-[(methoxyimino)-methyl]-2-oxo-1-azetidinesulphonic acid (E/Z mixture).

Elemental analysis for $C_{13}H_{14}N_3O_7SNa$: Calculated C 41.16, H 3.72, N 11.08%. Found: C 40.21, H 3.81, N 10.82%.

IR (Kbr, cm$^{-1}$): 3396, 3347, 1774, 1708, 1256.

EXAMPLE 5

240 mg of (3S,4S)-3-amino-4-carbamoyloxymethyl-2-oxo-1-azetidinesulphonic acid, 380 mg of 2-(2-amino-4-thiazolyl)-2-[(Z)-(2-propynyloxy)imino]-acetic acid 2-benzthiazolyl thioester and 200 mg of triethylamine are stirred at room temperature for 12 hours in 10 ml of methylene chloride. Thereafter, the precipitated product is filtered off and washed with methylene chloride. The solution of the crude triethylammonium salt (0.12 g) in 5 ml of methanol is treated with 0.24 ml of 2N sodium 2-ethylcaproate in ethyl acetate and thereafter with 25 ml of diethyl ether. There is obtained 0.08 g of (3S,4S)-3-[(Z)-2-(2-amino-4-thiazolyl)-2-[(2-propynyloxy)imino]acetamido]-4-carbamoyloxymethyl-2-oxo-1-azetidinesulphonic acid sodium salt.

$^1$H-NMR (d$_6$-DMSo, ppm): 9.24 (d, J=9 HZ, 1H); 7.21 (s, br., 2H), 6.73 (s, 1H), 6.49 (s, br., 2H), 5.27 (q, J=4.5 Hz and J=9 Hz, 1H), 4.67 (d, J=2.5 Hz, 2H), 4.0–4.3 (m, 3H), 3.46 (dd, J=2.5 Hz, 1H).

The 2-(2-amino-4-thiazolyl)-2-[(Z)-(2-propynyloxy)imino]-acetic acid 2-benzthiazolyl thioester used as the starting material can be prepared as follows:

112 ml of a 1.96N solution of sodium t-amylate in toluene and 22 g of propargyl chloride are added to a suspension of 43 g of ethyl 2-amino-4-thiazoleglyoxylate oxime in 300 ml of dimethylformamide, the temperature being held at 5°–10° C. by cooling. After 22 hours at 5° C., a further 28 ml of the sodium amylate solution and 5 g of propargyl chloride are added and the mixture is left to react at 5° C. for a further 24 hours. Thereafter, the mixture is poured into 600 ml of ethyl acetate and 1500 ml of ice-water. The mixture is extracted three times with 600 ml of ethyl acetate each time, the organic extracts are combined and evaporated. The residue is taken up in 100 ml of ethyl acetate/dichloromethane (1:4). The insoluble product is filtered off under suction and recrystallized from ethyl acetate. There are obtained 13.4 g of ethyl 2-amino-4-thiazoleglyoxylate (Z)-O-(2-(propynyl) oxime of melting point 170°–171° C. (decomposition). This oxime is saponified with 58.2 ml of 1N sodium hydroxide solution and 110 ml of methanol at 50° C. within 1.5 hours. After concentration to about half of the volume, 58.2 ml of 1N aqueous hydrochloric acid are added, the product crystallizing out upon standing at 0° C. The product is filtered off under suction and washed with water. There are obtained 8.45 g of 2-amino-4-thiazoleglyoxylic acid (Z)-O-(2-propynyl) oxime of melting point 136° C. (decomposition).

Elemental analysis for $C_8H_7N_3O_3S$ (225.22): Calculated: C 42.66, H 3.13, N 18.66, S 14.23%. Found: C 42.51, H 3.23, N 18.57, S 14.24%.

1.13 g of 2-amino-4-thiazoleglyoxylic acid (Z)-O-(2-propynyl) oxime are suspended in 60 ml of acetonitrile together with 2.4 ml of N-methylmorpholine and 5 g of dithio-bis-benzthiazole. A solution of 3 ml of triethyl phosphite in 8 ml of acetonitrile is added dropwise at room temperature while stirring within 4 hours. The mixture is subsequently stirred for a further 0.5 hour. The solution is evaporated to dryness and the residue is chromatographed on 300 g of silica gel (40–63 μm) using methylene chloride/ethyl acetate (9:1). There is obtained 0.2 g of 2-(2-amino-4-thiazolyl)-2-[(Z)-(2-propynyloxy)imino]-acetic acid 2-benzthiazolyl thioester as a crystalline evaporation residue.

$^1$H-NMR (d$_6$-NMR (d$_6$-DMSO, ppm): 7.5–8.4 ppm (m, 4H), 7.4 (s, br., 2H), 7.10 (s, 1H), 4.90 (d, J=2.5 Hz, 2H), 3.59 (dd, J=2.5 Hz, 1H).

EXAMPLE 6

In the same manner as described in Example 5, from 240 mg of (3S,4S)-3-amino-4-carbamoyloxymethyl-2-oxo-1-azetidinesulphonic acid and 380 mg of 2-(2-amino-4-thiazolyl)-2-[(Z)-(cyanomethoxy)imino]-acetic acid 2-benzthiazolyl thioester there are obtained 230 mg of (3S,4S)-3-[(Z)-2-[(cyanomethoxy)imino]-2-(2-amino-4-thiazolyl)acetamido]-4-carbamoyloxymethyl-2-oxo-1-azetidinesulphonic acid triethylamine salt. The product is recrystallized from acetonitrile.

$^1$H-NMR (d$_6$-DMSO, ppm): 9.42 (d, J=9.5 Hz, 1H), 7.3 (s, br., 2H), 6.90 (s, 1H), 6.5 (s, br., 2H), 5.31 (dd, J=4 Hz, J=9.5 Hz, 1H), 5.01 (s, 2H), 4–4.4 (m, 3H) 3.14 (q, J=7.3 Hz, 6H), 1.20 (t, J=7.3 Hz, 9H).

The 2-(2-amino-4-thiazolyl)-2-[(Z)-(cyanomethoxy)imino]-acetic acid 2-benzthiazolyl thioester used as the starting material can be prepared as follows:

22.7 g (0.1 mol) of allyl 2-(2-amino-4-thiazolyl)-2-(Z)-hydroxyimino-acetate are dissolved in 100 ml of dimethyl sulphoxide and 100 ml of acetone and the solutiion is treated with 25.2 g (0.4 mol) of potassium carbonate. The mixture is treated with 9.5 ml (0.15 mol) of chloroacetonitrile while stirring and the mixture is stirred at room temperature for 15 hours. The acetone is removed by distillation under reduced pressure, the residue is treated with 4 ml of ethyl acetate and washed neutral with ice-water. The phases are saparated. The ethyl acetate solution is evaporated under reduced pressure. The residue is dissolved in 150 ml of ethyl acetate while warming. After filtration, the filtrate is treated with 100 ml of ether. The product crystallizes out. After cooling, the crystals are filtered off and washed with ether. There are obtained 11.1 g (41.7%) of allyl 2-(2-(amino-4-thiazolyl)-2-[(Z)-(cyanomethoxy)imino]-acetate of melting point 148°–149° C.

The same product can also be prepared as follows:

4.54 g of allyl 2-(2-amino-4-thiazolyl)-2-(Z)-hydroxyimino-acetate are dissolved in 100 ml of methylene chloride and the solution is treated with 1.9 ml of chloroacetonitrile and 680 mg of tetrabutylammonium hydrogen sulphate. 10 ml of 4N sodium hydroxide solution are then added dropwise during 1 hour at room temperature while stirring vigorously. The mixture is stirred for a further 1.5 hours, the organic phase is then separated, washed neutral with water, dried and evaporated. The residue is recrystallized from 30 ml of ethanol, there being obtained 2.2 g (41.3%) of allyl 2-(2-amino-4-thiazolyl)-2-[(Z)-cyanomethoxy)imino]-acetate of melting point 147°–148° C.

2.66 g (0.01 mol) of allyl 2-(2-amino-4-thiazolyl)-2-[(Z)-(cyanomethoxy)imino]-acetate in 100 ml of ethyl acetate are treated dropwise while stirring with 17.73 mg (0.0001 mol) of palladium chloride and 0.083 ml (0.0005mol) of triethyl phosphite. After stirring for 5 minutes, 5.5 ml (0.011 mol) of sodium 2-ethylcaproate solution (2N in ethyl acetate) are added thereto. After stirring for about 0.5 hour, crude 2-(2-amino-4-thiazolyl)-2-[(Z)-(cyanomethoxy)imino]-acetic acid sodium salt precipitates out. The mixture is stirred at room temperature for a further 2 hours and subsequently extracted twice with 50 ml of water each time and once with 30 ml of saturated aqueous sodium bicarbonate solution. The aqueous phases are extracted once with ethyl acetate, then combined, adjusted to pH 2 with 2N aqueous hydrochloric acid and evaporated to dryness. After the addition of methanol/benzene and repeated evaporation, the residue is dissolved in 50 ml of methanol. The sodium chloride formed is filtered off. Crystallization occurs after cooling. The crystals obtained are filtered off and washed with methanol and ether. Ther are obtained 1.42 g (58.6%) of 2-(2-amino-4-thiazolyl)-2-[(Z)-(cyanomethoxy)imino]-acetic acid of melting point 140°–142° C. (decomposition).

Elemental analysis for $C_7H_6N_4O_3S$. 0.5 $CH_3OH$ (242.231): Calculated: C 37.19, H 3.33, H 23.13, S 13.24% Found: C 37.19, H 2.92, N 23.06, S 13.31%

The NMR spectrum agrees with the given structure.

The working-up can also be carried out as follows:

The ethyl acetate suspension obtained in the above reaction is evaporated under reduced pressure. The residue is treated with 2.25 ml of 4N aqueous hydrochloric acid and 30 ml of methanol and the mixture is evaporated under reduced pressure. The residue is dissolved in 60 ml of methanol while warming, insoluble material is removed by filtration and the filtrate is cooled. 1.65 g of 2-(2-amino-4-thiazolyl)-2-[(Z)-(cyanomethoxy)imino]-acetic acid crystallize out. The mother liquor is evaporated and the residue is dissolved in 20 ml of methanol while warming. Insoluble material is removed by filtration. After cooling, the solution yields a further 0.2 g of product, the total yield being 1.85 g (76.3%).

The 2-(2-amino-4-thiazolyl)-2-[(Z)-(cyanomethoxy)imino]-acetic acid can also be prepared as follows:

2.66 g (0.01 mol) of allyl 2-(2-amino-4-thiazolyl)-2-[(Z)-(cyanomethoxy)imino]-acetic in 100 ml of ethyl acetate are treated while stirring with 17.73 mg (0.001 mol) of palladium chloride and 0.083 ml (0.0005 mol) of triethyl phosphate. After stirring for 10 minutes, 0.9 g (0.11 mol) of sodium acetate is added thereto. The reaction occurs after the addition of 1 ml of water and crude 2-(2-amino-4-thiazolyl)-2-[(Z)-(cyanomethoxy)imino]-acetic acid sodium salt precipitates out. The mixture is stirred at room temperature for a further 24 hours, subsequently extracted twice with 30 ml of water each time, the aqueous solution is extracted once with ether and subsequently adjusted to pH 2 with 2N aqueous hydrochloric acid. After evaporation to dryness, the residue is dissolved in 50 ml of methanol, filtered and cooled. There are obtained 1.1 g (45.4%) of 2-(2-amino-4-thiazolyl)-2-[(Z)-(cyanomethoxy)imino]-acetic acid of melting point 140°–142° C. (decomposition).

A third method for the preparation of 2-(2-amino-4-thiazolyl)-2-[(Z)-(cyanomethoxy)imino]-acetic acid is as follows:

2.66 g (0.01 mol) of allyl 2-(2-amino-4-thiazolyl)-2-[(Z)-(cyanomethoxy)imino]-acetate in 100 ml of ethyl acetate are treated while stirring with 17.73 mg (0.0001 mol) of palladium chloride and 0.083 ml (0.0005 mol) of triethyl phosphite. After the addition of 1.54 ml (0.011 mol) of triethylamine, the mixture is stirred at room temperature for 24 hours. Crude 2-(2-amino-4-thiazolyl)-2-[(Z)-(cyanomethoxy)imino]-acetic acid triethylamine salt precipitates out. The filtered-off crude salt (2.9 g) is dissolved in 30 ml of methanol. The solution is adjusted to pH 3 with 2N aqueous hydrochloric acid. Crystallization occurs. The crystals obtained are filtered off and washed with methanol and ether. There are obtained 1.24 g (51.2%) of 2-(2-amino-4-thiazolyl)-2-[(Z)-(cyanomethoxy)imino]-acetic acid of melting point 140°–142° C. (decomposition).

1.85 g of 2-(2-amino-4-thiazolyl)-2-[(Z)-(cyanomethoxy)imino]-acetic acid are suspended in 90 ml of acetonitrile together with 1.02 ml of N-methylmorpholine and 2.81 g of 2,2-dithio-bis-benzthiazole. A solution of 1.64 ml of triethyl phosphite in 20 ml of acetonitrile is added dropwise at room temperature while stirring within 1 hour. The mixture is subsequently stirred at room temperature for a further 2 hours. The mixture is filtered and the filtrate is evaporated under reduced pressure. The residue is dissolved in 100 ml of ethyl acetate, a small amount of insoluble material is filtered off and the filtrate is evaporated to a volume of 40 ml. After cooling, the crystals obtained are filtered off and washed with ethyl acetate. There are obtained 1.2 g of 2-(2-amino-4-thiazolyl)-2-[(Z) -(cyanomethoxy)imino]-acetic acid 2-benzthiazolyl thioester of melting point 155°–156° C. (decomposition). The mother liquor is evaporated. After the addition of methanol, there is obtained a further 0.4 g of products of melting point 155°–156° C. (decomposition).

A further method for the preparation of the same compound is as follows:

2.66 g (0.01 mol) of allyl 2-(2-amino-4-thiazolyl)-2-[(Z)-(cyanomethoxy)imino]-acetate in 100 ml of ethyl acetate are treated while stirring with 17.73 mg (0.0001 mol) of palladium chloride and 0.083 ml (0.0005 mol) of triethyl phosphite. After the addition of 1.2 ml (0.011 mol) of N-methylmorpholine, the mixture is stirred at room temperature for 24 hours. Crude 2-(2-amino-4-thiazolyl)-2-[(Z)-(cyanomethoxy)imino]-acetic acid N-methylmorpholine salt precipitates out. The filtered-off crude salt (3.1 g, 84.3%) is suspended in 100 ml of acetonitrile together with 0.47 ml of N-methylmorpholine and 3.2 g of 2,2-dithio-bisbenzthiazole. A solution of 2.42 ml of triethyl phosphite in 20 ml of acetonitrile is added dropwise at room temperature while stirring within 1 hour. The mixture is subsequently stirred at room temperature for a further 2 hours. The mixture is filtered and the filtrate is evaporated under reduced pressure. The residue is dissolved in 100 ml of ethyl acetate, a small amount of insoluble material is filtered off and the filtrate is evaporated to a volume of 40 ml. After cooling, the crystals obtained are filtered off and washed with ethyl acetate. There are obtained 1.8 g of 2-(2-amino-4-thiazolyl)-2-[(Z)-(cyanomethoxy)imino]-acetic acid 2-benzthiazolyl thioester of melting point 160°–161° C. (decomposition).

EXAMPLE 7

In the same manner as described in Example 5, from 220 mg of rac,cis-3-amino-4-methoxycarbonyl-2-oxo-1-azetidinesulphonic acid and 380 mg of 2-(2-amino-4-thiazolyl)-2-[(Z)-(cyanomethoxy)imino]-acetic acid 2-benzthiazolyl thioester there are obtained 350 mg of rac,cis-3-[2-(2-amino-4-thiazolyl)-2-(Z)-[(cyanomethoxy)imino]acetamido]-4-methoxycarbonyl-2-oxo-1-azetidinesulphonic acid triethylamine salt. The product is recrystallized from nitromethane, melting point 208°–210° C. (decomposition).

Elemental analysis for $C_{12}H_{12}N_6O_8S_2 \cdot C_6H_{15}N$ (533.58): Calculated: C 40.52, H 5.10, N 18.38, S 12.02%. Found: C 40.21, H 5.22, N 18.20, S 11.91%.

EXAMPLE 8

In the same manner as described in Example 5, from 180 mg of (3S,4S)-3-amino-4-methyl-2-oxo-1-azetidinesulphonic acid and 380 mg of 2-(2-amino-4-thiazolyl)-2-[(Z)-(cyanomethoxy)imino]-acetic acid-2-benzthiazolyl thioester there are obtained 400 mg (3S,4S)-3-[2-(2-amino-4-thiazolyl)-2-(Z)-[(cyanomethoxy)imino]acetamido]-4-methyl-2-oxo-1-azetidinesulphonic acid triethylamine salt. The product is recrystallized from acetonitrile, melting point 158°–160° C.

Elemental analysis for $C_{11}H_{12}N_6O_6S_2 \cdot C_6H_{15}N$ (489.57): Calculated: C 41.71, H 5.56, N 20.03, S 13.10%. Found: C 41.20, H 5.89, N 19.73, S 13.00%.

EXAMPLE 9

7.7 g of 2-chloro-1-methyl-pyridinium iodide are added to a solution of 6.8 g of 2-(2-amino-4-thiazolyl)-2-[(Z)-(2-iodoethoxy)imino]-acetic acid, 4.8 g of (3S,4S)-3-amino-4-carbamoyloxymethyl-2-oxo-1-azetidinesulphonic acid and 8.4 g of triethylamine in 50 ml of dimethylformide and the mixture is stirred for 2 hours. After removal of the solvent under reduced pressure at about 25° C., the residue is taken up in 250 ml of water and washed with 100 ml of ethyl acetate and twice with 100 ml of dichloromethane. After the addition of 20.3 g of tetra-n-butylammonium hydrogen sulphate, the mixture is adjusted to pH 6–7 using 70 ml of saturated sodium bicarbonate solution and extracted four times with 100 ml of dichloromethane each time. The combined extracts are washed with 50 ml of water. The product is then precipitated by the addition of 7.5 ml of formic acid. After washing with acetone and ether, there are obtained 5.6 g of (3S,4S)-3-[(Z)-2-(2-amino-4-thiazolyl)-2-[(2-iodoethoxy)imino]acetamido]-4-carbamoyloxymethyl-2-oxo-1-azetidinesulphonic acid.

0.5 g of this crude product is brought into solution with 5 ml of water and 75 mg of sodium bicarbonate and subjected to reverse-phase chromatography on a column of silica gel using water for the elution. After lyophilization, there are obtained 200 mg of pure (3S,4S)-3-[(Z)-2-(2-amino-4-thiazolyl)-2-[(2-iodoethoxy)imino]acetamido]-4-carbamoyloxymethyl-2-oxo-1-azetidinesulphonic acid sodium salt.

Elemental analysis for C$_{12}$H$_{14}$IN$_6$O$_8$S$_2$Na (584.29): Calculated: C 24.67, H 2.42, I 21.72, N 14.38%. Found: C 24.79, H 2.45, I 21.29, N 14.25%.

The 2-(2-amino-4-thiazolyl)-2-[(Z)-(2-iodoethoxy)imino]-acetic acid used as the starting material can be prepared as follows:

80.55 g of ethyl 2-(2-amino-4-thiazolyl)-2-[(Z)-(2-bromoethoxy)imino]-acetate and 187.4 g of sodium iodide are boiled under reflux in 1.5 l of methyl ethyl ketone for 1.5 hours. After removal of the solvent by evaporation, the residue is partitioned between 0.6 l of water and 0.2 l of ethyl acetate, the aqueous phase is back-extracted twice with 0.2 l of ethyl acetate each time, the organic extracts are thereupon combined, washed with 0.2 l of aqueous 15% sodium chloride solution, dried and evaporated. The residue is recrystallized from 0.7 l of toluene. 83.5 g of ethyl 2-(2-amino-4-thiazolyl)-2-[(Z)-(2-iodoethoxy)imino]acetate are obtained.

83.5 g of ethyl 2-(2-amino-4-thiazolyl)-2-[(Z)-(2-iodoethoxy)imino]-acetate are saponified by boiling at reflux for 1 hour with 240 ml of aqueous 1N sodium hydroxide solution in 500 ml of methanol. Thereafter, the mixture is evaporated under reduced pressure to about one third of the volume, 240 ml of aqueous 1N hydrochloric acid are added thereto and the precipitated acid is filtered off under suction. For purification, this acid is treated with 700 ml of methanol in an ultrasonics bath. The insoluble product is filtered off under suction at 0° C. and dried. There are thus obtained 64.7 g of 2-(2-amino-4-thiazolyl)-2-[(Z)-(2-iodoethoxy)imino]-acetic acid of melting point 182° C. (decomposition).

$^1$H-NMR (d$_6$-DMSO, ppm): 7.3 (br., 2H), 6.78 (s, 1H), 4.31 (t, J=6.5 Hz, 2H), 3.29 (t, J=6.5 Hz, 2H).

EXAMPLE 10

280 mg of (3S,4S)-3-[(Z)-2-(2-amino-4-thiazolyl)-2-[(2-iodoethoxy)imino]acetamido]-4-carbamoyloxymethyl-2-oxo-1-azetidinesulphonic acid are stirred at room temperature for 12 hours in 2 ml of pyridine and 2 ml of acetonitrile. The product which precipitates out is filtered off under suction, washed with acetonitrile and dried. There are obtained 215 mg of (3S,4S)-3-[(Z)-2-(2-amino-4-thiazolyl)-2-[[2-(1-pyridinio)ethoxy]imino]acetamido]-4-carbamoyloxymethyl-2-oxo-1-azetidinesulphate.

$^1$H-NMR (d$_6$-DMSO, ppm): 9.25 (d, J=9.5 Hz, 1H), 8.96 (m, 2H), 8.63 (m, 1H), 8.14 (m, 2H) 7.2 (s, br., 2H), 6.74 (s, 1H), 6.51 (s, br., 2H), 5.22 (dd, J=4.5 Hz and 9.5 Hz, 1H), 4.89 (m, 2H), 4.58 (m, 2H), 4.26–3.9 (m, 3H).

The same compound is also obtained in a manner analogous to that described in Example 9 from (Z)-2-(2-amino-4-thiazolyl)-2-[(Z)-[2-(1-pyridinio)ethoxy]imino]-acetic acid and (3S,4S)-3-amino-4-carbamoyloxymethyl-2-oxo-1-azetidinesulphonic acid.

The (Z)-2-(2-amino-4-thiazolyl)-2-[(Z)-[2-(1-pyridinio)ethoxy]imino]-acetic acid referred to in the preceding paragraph can be prepared as follows:

32 g of ethyl 2-(2-aminothiazol-4-yl)-2-(2-bromoethoxyimino)-acetate are hydrolyzed in 200 ml of methanol with 200 ml of 1N aqueous sodium hydroxide solution by heating to 50° C. for 1 hour. By the addition of 200 ml of 1N aqueous hydrochloric acid to the cooled solution there precipitate out 24 g of 2-(2-aminothiazol-4-yl)-2-(2-bromoethoxyimino)-acetic acid of melting point 190° C. (decomposition).

1.8 g of 2-(2-aminothiazol-4-yl)-2-(2-bromoethoxyimino)-acetic acid are heated to 80° C. for 1 hour in 20 ml of pyridine. Upon cooling there separates a resinous precipitate which is crystallized using ethyl acetate. There are obtained 1.2 g of (Z)-2-(2-amino-4-thiazolyl)-2-[(Z)-[2-(1-pyridinio)ethoxy]imino]-acetic acid as a hygroscopic product.

$^1$H-NMR (DMSO, ppm): 9.10 (d), 8.62 (d) and 8.18 (t) (pyridinium-H), 6.88 (s, thiazole-H), 6.21 (s, br., —NH$_2$), 5.0 and 4.69 (2×m, br.,

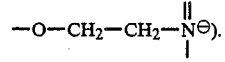

EXAMPLE 11

In the same manner as described in Example 9, from 12 g of (3S,4S)-3-amino-4-carbamoyloxymethyl-2-oxo-1-azetidinesulphonic acid and 2-(2-amino-4-thiazolyl)-2-[(Z)-[2-(methylsulphonyl)ethoxy]imino]-acetic acid there are obtained 1.15 g of (3S,4S)-3-[(Z)-2-(2-amino-4-thiazolyl)-2-[[2-(methylsulphonyl)ethoxy]imino]acetamido]-4-carbamoyloxymethyl-2-oxo-1-azetidinesulphonic acid.

Elemental analysis for C$_{13}$H$_{18}$N$_6$O$_{10}$S$_3$.0.1C$_3$H$_8$O (isopropanol): Calculated: C 30.69, H 3.64, N 16.15, S 18.48%. Found: C 30.62, H 3.51, N 15.99, S 18.24%.

The 2-(2-amino-4-thiazolyl)-2-[(Z)-[2-(methylsulphonyl)ethoxy]imino]-acetic acid used as the starting material can be prepared as follows:

17.06 g of 2-(2-amino-4-thiazolyl)-2-[(Z)-(2-iodoethoxy)imino]-acetic acid, 4.2 g of sodium bicarbonate and 6.1 g of sodium methylsulphinate are reacted at room temperature for 70 hours in 100 ml of dimethylformamide. After removal of the solvent by evaporation, the residue is dissolved in 200 ml of water, the solution is washed four times with 100 ml of ethyl acetate each time and thereupon absorbed on 200 ml of DOWEX 1 (ion exchange resin; OH form). Elution is carried out with 1N aqueous acetic acid, there being obtained 11.5 g of a product which is crystallized by means of 150 ml of isopropanol. There are obtained 8.9 g of 2-(2-amino-4-thiazolyl)-2-[(Z)-[2-(methylsulphonyl)ethoxy]imino]-acetic acid of melting point 167°–169° C. (decomposition).

$^1$H-NMR (d$_6$-DMSO, ppm): 7.8 (s, br., 2H), 6.92 (s, 1H), 4.42 (t, J=6 Hz, 2H), 3.50 (t, J=6 Hz, 2H), 2.98 (s, 3H).

EXAMPLE 12

In the same manner as described in Example 9, from 1.2 g of (3S,4S)-3-amino-4-carbamoyloxymethyl-2-oxo-1-azetidinesulphonic acid and 1.4 g of 2-(2-amino-4-thiazolyl)-2-[(Z)-(2-imidazol-1-yl-ethoxy)imino]-acetic acid there is obtained 0.3 g of (3S,4S)-3-[(Z)-2-(2-amino-4-thiazolyl)-2-[(2-imidazol-1-yl-ethoxy)imino]acetamido]-4-carbamoyloxymethyl-2-oxo-1-azetidinesulphonic acid hydrochloride.

$^1$H-NMR (d$_6$-DMSO, ppm): 9.45 (d, J=9.5 Hz, 1H), 9.09 (m, 1H), 7.77 (m, 1H), 7.71 (m, 1H), 6.94 (s, 1H), 6.55 (s, br., >2H); 5.29 (dd, J=4 Hz, J=9.5 Hz, 1H), 4.0–4.7 (m, >6H).

The 2-(2-amino-4-thiazolyl)-2-[(Z)-(2-imidazol-1-yl-ethoxy)imino]-acetic acid used as the starting material can be prepared as follows:

16.1 g of ethyl 2-(2-amino-4-thiazolyl)-2-[(Z)-(2-bromoethoxy)imino]-acetate and 17 g of imidazole are boiled under reflux for 4 hours in 160 ml of acetonitrile. The mixture is evaporated to dryness under reduced pressure, the residue is taken up in 150 ml of water, 25 ml of aqueous 3N sodium hydroxide solution and 100 ml of ethyl acetate and the aqueous phase is extracted twice with 100 ml of ethyl acetate each time. The organic phase are combined, washed with a small amount of water and evaporated. The residue is saponified at 50° C. for 1.5 hours with 100 ml of aqueous 1N sodium hydroxide solution and 100 ml of methanol. After the addition of 100 ml of 1N aqueous hydrochloric acid, the mixture is evaporated. The evaporation residue is crystallized using 250 ml of methanol and the crystallizate is suction filtered. There are obtained 13.2 g of crude 2-(2-amino-4-thiazolyl)-2-[(Z)-(2-imidazol-1-yl-ethoxy)imino]-acetic acid. For purification, a solution of 11 g of crude product in 100 ml of water is adsorbed on 200 ml of DOWEX 50 W (ion exchange resin; H+ form). The product is recovered by elution with 2.5% aqueous ammonia solution. After evaporation of the solvent, the product is crystallized using methanol. There are obtained 5.6 g of 2-(2-amino-4-thiazolyl)-2-[(Z)-(2-imidazol-1-yl-ethoxy)imino]-acetic acid of melting point 166° C. (decomposition).

Elemental analysis for $C_{10}H_{11}N_5O_3S$ (281.29): Calculated: C 42.70, H 3.94, N 24.90, S 4.40%. Found: C 42.56, H 4.18, N 24.77, S 11.29%.

EXAMPLE 13

In the same manner as described in Example 9, from 1.87 g of (3S,4S)-3-amino-4-carbamoyloxymethyl-2-oxo-1-azetidinesulphonic acid and 2 g of 2-(2-amino-4-thiazolyl)-2-[(Z)-(2-azidoethoxy)imino]-acetic acid there are obtained 2.2 g of (3S,4S)-3-[(Z)-2-(2-amino-4-thiazolyl)-2-[(2-azidoethoxy)imino]acetamido]-4-carbamoyloxymethyl-2-oxo-1-azetidinesulphonic acid.

$^1$H-NMR ($d_6$-DMSO, ppm): 9.38 (d, J=9.5 Hz, 1H), 8.2 (s, br., 4–5H), 6.98 (s, 1H), 5.33 (dd, J=4 Hz, J=9.5 Hz, 1H), 3.9–4.4 (m, 5H), 3.65 (dd, J=5 Hz, 2H).

The 2-(2-amino-4-thiazolyl)-2-[(Z)-(2-azidoethoxy)imino]-acetic acid used as the starting material can be prepared as follows:

1 g of ethyl 2-(2-amino-4-thiazolyl)-2-[(Z)-(2-bromoethoxy)imino]-acetate in 20 ml of dimethylformamide is warmed to 50° C. for 12 hours with 9.5 g of sodium azide. The mixture is diluted with ethyl acetate, washed three times with water, dried over magnesium sulphate and evaporated. After recrystallization from acetone/isopropanol, there is obtained 0.85 g of ethyl 2-(2-amino-4-thiazolyl)-2-[(Z)-(2-azidoethoxy)imino]-acetate of melting point 123°–124° C.

8.1 g of ethyl 2-(2-amino-4-thiazolyl)-2-[(Z)-(2-azidoethoxy)imino]-acetate are dissolved in 150 ml of methanol and 45 ml of 2N aqueous sodium hydroxide solution. After 20 hours, 50 ml of water are added thereto. The methanol is then removed in vacuo. The aqueous solution is treated with 90 ml of 1N aqueous hydrochloric acid and concentrated to dryness. The residue is taken up in 200 ml of dimethylformamide. The sodium chloride is removed by filtration and the solution is concentrated to 50 ml. The acid is precipitated by the addition of acetonitrile. There are obtained 6.5 g of 2-(2-amino-4-thiazolyl)-2-[(Z)-(2-azidoethoxy)imino]-acetic acid. Yield: 6.5 g of melting point 180° C.

EXAMPLE 14

0.7 g of (3S,4S)-3-[(Z)-2-(2-amino-4-thiazolyl)-2-[(2-azidoethoxy)imino]acetamido]-4-carbamoyloxymethyl-2-oxo-1-azetidinesulphonic acid is dissolved in 15 ml of water together with 0.6 g of tetrabutylammonium hydrogen sulphate and 4 ml of saturated aqueous sodium bicarbonate solution. The mixture is extracted three times with dichloromethane, the extract is evaporated to dryness under reduced pressure, the residue is taken up in 25 ml of methanol and hydrogenated at room temperature in the presence of 1 g of 5% palladium/carbon for 1 hour. The mixture is then filtered, the filtrate is treated with 0.2 ml of formic acid and subsequently evaporated. The residue is triturated successively with 50 ml of isopropanol, 25 ml of ether and 10 ml of methanol and in each case filtered off under suction. Thereafter, the residue is taken up in 2 ml of water, filtered over a small amount of active carbon and the product is precipitated by the addition of 15 ml of acetonitrile. The precipitate (62 mg) is filtered off under suction and the filtrate is evaporated. By trituration of the residue in 1 ml of acetonitrile there are obtained a further 54 mg of crystalline product. The total yield is 116 mg of (3S,4S)-3-[(Z)-2-[(2-aminoethoxy)imino]-2-(2-amino-4-thiazolyl)acetamido]-4-carbamoyloxymethyl-2-oxo-1-azetidinesulphonic acid.

$^1$H-NMR ($d_6$-DMSO, ppm): 9.08 (d, J=9 Hz, 1H), 7.7 (s, br., 3H); 7.22 (s, br., 2H), 6.81 (s, 1H); 6.53 (s, br., 2H), 5.27 (dd, J=4.5 Hz and 9 Hz, 1H), 4.0–4.35 (m, 5H), 3.13 (m, 2H).

EXAMPLE 15

358 mg (1.5 mmol) of (3S,4S)-3-amino-4-carbamoyloxymethyl-2-oxo-1-azetidinesulphonic acid in 15 ml of methylene chloride and 10 ml of methanol are treated with 804 mg (1.65 mmol) of 2-(2-amino-4-thiazolyl)-2-[(Z)-(1H-tetrazol-5-yl-methoxy)imino]-acetic acid 2-benzthiazolyl thioester and 0.23 ml (1.65 mmol) of triethylamine. After 2 days at room temperature, 2 ml of 2N sodium 2-ethylcaproate solution in ethyl acetate are added thereto. The crystals obtained are filtered off and washed with methylene chloride. 660 mg (82%) of (3S,4S)-3-[(Z)-2-(2-amino-4-thiazolyl)-2-[(1H-tetrazol-5-yl-methoxy)imino]acetamido]-4-carbamoyloxymethyl-2-oxo-1-azetidinesulphonic acid disodium salt are obtained.

Elemental analysis for $C_{12}H_{12}N_{10}O_8S_2Na_2$: Calculated: C 26.97, H 2.26, N 26.21%. Found: C 26.93, H 2.15, N 25.95%.

IR (KBr, cm$^{-1}$) 1766, 1717, 1670, 1616.

$^1$H-NMR ($d_6$-DMSO, ppm): 4.05 (2H, m, CH—CH$_2$), 4.35 (1H, m, CH—CH$_2$), 5.21 (2H, s, N—O—CH$_2$), 5.29 (1H, dd, J=5 and 9 Hz, NH—CH), 6.5–6.9 (2H, br., NH$_2$), 6.68 (1H, s, H-thiazole), 7.28 (2H, s, NH$_2$), 9.71 (1H, d, J=9 Hz NH—CH).

The 2-benzthiazolyl thioester used as the starting material can be prepared as follows:

54 g of ethyl 2-(2-amino-4-thiazolyl)-2-(Z)-hydroxyimino-acetate are dissolved in 500 ml of dimethylformamide. After the addition of 138 g of potassium carbonate, there are added dropwise within 1 hour 47 ml of chloroacetonitrile and the mixture is then stirred at room temperature for 20 hours. The dark solution obtained is poured into ice-water and extracted with ethyl acetate. The organic phase is washed with water, treated with active carbon, dried over magnesium sulphate and concentrated. After recrystallization from toluene, there are obtained 38 g of ethyl 2-(2-amino-4-thiazolyl)-2-[(Z)-(cyanomethoxy)imino]-acetate of melting point 167°–168° C.

5.0 g of ethyl 2-(2-amino-4-thiazolyl)-2-[(Z)-(cyanomethoxy)imino]-acetate are heated to 60° C. for 48 hours while stirring together with 1.95 g of sodium azide and 1.6 g of ammonium chloride in 50 ml of dimethylformamide. The mixture is taken up in water/ethyl acetate. The ethyl acetate phase is washed twice with a small amount of water. The combined aqueous phases are concentrated to dryness, the residue is dissolved in 50 ml of 1N aqueous sodium hydroxide solution and stored at room temperature for 1 hour. The mixture is subsequently diluted with 50 ml of water and the solution is concentrated to 50 ml. The product crystallizes after the addition of 50 ml of aqueous 1N hydrochloric acid. There are obtained 3.9 g of 2-(2-amino-4-thiazolyl)-2-[(Z)-(1H-tetrazol-5-yl-methoxy)imino]-acetic acid of melting point 151°–152° C. The water content is 6.96%.

Elemental analysis for $C_7H_7N_7O_3S$: Calculated: C 31.23, H 2.62, N 36.42%. Found: C 31.26, H 2.95, N 36.24%.

6.75 g of 2-(2-amino-4-thiazolyl)-2-[(Z)-(1H-tetrazol-5-yl-methoxy)imino]-acetic acid and 25 g of 2,2-dithio-bis-benzthiazole are suspended in 300 ml of acetonitrile. After the addition of 24.3 ml of N-ethyldiisopropylamine, there are added dropwise while stirring at room temperature within 4 hours 14.1 ml of triethyl phosphite in 40 ml of acetonitrile. The crystals formed are filtered off and dried. There are obtained 12 g of 2-(2-amino-4-thiazolyl)-2-[(Z)-(1H-tetrazol-5-yl-methoxy)imino]-acetic acid 2-benzthiazolyl thioester of melting point 150°–151° C.

EXAMPLES 16-19

(16) 478 mg (2 mmol) of (3S,4S)-3-amino-4-carbamoyloxymethyl-2-oxo-1-azetidinesulphonic acid in 30 ml of water/acetone (1:1) are treated with 185 mg of sodium bicarbonate and 1015 mg (2.2 mmol) of 2-(2-amino-4-thiazolyl)-2-[[(Z)-(1-piperidinecarbonyl)methoxy]imino]-acetic acid 2-benzthiazolyl thioester. After 18 hours, the acetone is removed by evaporation. The crystals are filtered off under suction. The aqueous solution is chromatographed on MCI gel using water and water/methanol (9:1) for the elution. There are obtained 765 mg (69%) of (3S,4S)-3-[(Z)-2-(2-amino-4-thiazolyl)-2-[[(1-piperidinecarbonyl)methoxy]imino]acetamido]-4-carbamoyloxymethyl-2-oxo-1-azetidinesulphonic acid sodium salt.

Elemental analysis for $C_{17}H_{22}N_7O_9S_2Na$: Calculated: C 36.76, H 3.99, N 17.65, S 11.54%. Found: C 36.96, H 4.12, N 17.62, S 11.54%.

NMR (d$_6$-DMSO, ppm): 1.55 (6H, m 3×CH$_2$), 3.32 (4H, m, 2×N—CH$_2$), 4.10 (2H, m, —CH$_2$—O—CONH$_2$), 4.27 (1H, m, CH—CH$_2$—OCOHN$_2$), 4.77 (2H, 2d, J=15 Hz, N—O—CH$_2$), 5.30 (1H, dd, J=5.5 and 10 Hz, NH—CH); 6.30 (2H, br. OCONH), 6.80 (1H=H-thiazole), 7.25 (2H, s, NH$_2$), 9.40 (1H, d, J=10 Hz, NH).

In the same manner there can be manufactured:

(17) (3S,4S)-3-[(Z)-2-(2-Amino-4-thiazolyl)-2-[[[(hexahydro-1H-azepin-1-yl)-carbonyl]methoxy]imino]acetamido]-4-carbamoyloxymethyl-2-oxo-1-azetidinesulphonic acid sodium salt.

Elemental analysis for $C_{18}H_{24}N_7O_9S_2Na$: Calculated: C 37.96, H 4.25, N 17.22, S 11.26%. Found: C 38.34, H. 4.11, N 17.35, S 11.12%.

IR (KBr, cm$^{-1}$): 1767, 1722, 1630, 1533.

NMR (d$_6$-DMSO, ppm): 1.5–1.75 (8H, m, 4×CH$_2$), 3,40 (4H, m, 2×N—CH$_2$), 4.05 (2H, m, CH$_2$—O—CONH$_2$), 4.25 (1H, m, CH—CH$_2$—OCONH$_2$), 4.80 (2H, 2d, J=15 Hz, N—O—CH$_2$), 5.30 (1H, dd, J=5 and 10 Hz, NH—CH), 6.50 (2H, br., NH$_2$), 6.78 (1H, s, H-thiazole), 7.21, s, NH$_2$), 9.40 (1H, d, J=10 Hz, NH).

(18) (3S,4S)-3-[(Z)-2-(2-Amino-4-thiazolyl)-2-[[(1-methyl-1H-tetrazol-5-yl)methoxy]imino]acetamido]-4-carbamoyloxymethyl-2-oxo-1-azetidinesulphonic acid sodium salt.

Elemental analysis for $C_{13}H_{15}N_{10}O_8S_2Na$: Calculated: C 29.66, H 2.87, N 26.61, S 12.18%. Found: C 31.85, H 3.25, N 27.36, S 11.95%.

IR (KBr, cm$^{-1}$): 1770, 1721, 1678, 1635.

$^1$H-NMR (d$_6$-DMSO, ppm): 3.9–4.2 (3H, m, CH—CH$_2$), 4.10 (3H, s, N—CH$_3$), 4.9 (2H, br., NH$_2$), 5.31 (2H, dd, J=5 and 9 Hz, NH—CH), 5.55 (2H, 2d, J=15 Hz, N—O—CH$_2$) 6.6 (2H, br., NH$_2$), 6.83 (1H, s, H-thiazole) 9.40 (1H, d, J=9 Hz, NH—CH).

(19) (3S,4S)-3-[(Z)-2-(Amino-4-thiazolyl)-2-[[(diethylcarbamoyl)methoxy]imino]acetamido]-4-carbamoxyloxymethyl-2-oxo-1-azetidinesulphonic acid sodium salt.

Elemental analysis for $C_{16}H_{22}N_7O_9S_2Na$ Calculated: C 35.26, H 4.08, N 18.04, S 11.80%. Found: C 35.74, H 4.06, N 18.03, S 11.81%.

IR (KBr, cm$^{-1}$); 1767, 1722, 1671, 1631.

$^1$H-NMR (d$_6$-DMSO, ppm): 1.10 (6H, m, 2×CH$_3$), 3.30 (4H, m, 2×N—CH$_2$), 4.10 (3H, m, CH—CH$_2$), 4.85 (2H, s, N—O—CH$_2$), 5.30 (1H, dd, J=5 and 9 Hz, NH—CH), 6.45 (2H, br., NH$_2$), 6.85 (1H, s, H-thiazole), 7.15 (2H, br., NH$_2$), 9.35 (1H, d, J=9 Hz, NH—CH).

The 2-benzothiazolyl thioesters used as the starting materials in Examples 16–19 can be prepared as follows:

(16) 83.8 g of ethyl 2-(2-amino-4-thiazolyl)-2-(Z)-hydroxyimino-acetate, 94.4 g of N-chloroacetylpiperidine, 202.5 ml of N-ethyldiisopropylamine and 87.6 g of sodium iodide are stirred at room temperature for 12 hours in 1420 ml of acetonitrile. The mixture is diluted with 7 l of ethyl acetate, washed with water, dried over magnesium sulphate and concentrated to a small volume. The substance which crystallizes ot is filtered off and dried. There are obtained 77.2 g of ethyl 2-(2-amino-4-thiazolyl)-2-[(Z)-[(1-piperidinecarbonyl)methoxy]imino]-acetate of melting point 151°–152° C.

77.2 g of ethyl 2-(2-amino-4-thiazolyl)-2-[(Z)-[(1-piperidinecarbonyl)methoxy]imino]-acetate are dissolved in 3 l of methanol and 265 ml of water and the solution is treated with 250 ml of 1N aqueous sodium hydroxide solution. The saponification is complete after 48 hours. 500 ml of water are added thereto and the methanol is removed under reduced pressure. The aqueous solution is washed with ethyl acetate, treated with 250 ml of 1N aqueous hydrochloric acid and concentrated to half of the volume. The acid which crystallizes out is filtered off and dried. There are obtained 55.3 g of 2-(2-amino-4-thiazolyl)-2-[(Z)-[(1-piperidinecarbonyl)methoxy]imino]-acetic acid of melting point 177° C.

48 g of 2-(2-amino-4-thiazolyl)-2-[(Z)-[(1-piperidinecarbonyl)methoxy]imino]-acetic acid and 61.6 g of 2,2-dithio-bis-benzthiazole are suspended in 2.3 l of acetonitrile and treated with 25.5 ml of N-methylmorpholine. 46.2 ml of triethyl phosphite in 300 ml of acetonitrile are added dropwise thereto within 4 hours at 0° C. while stirring. The crystalline thioester is filtered off and dried. There are obtained 64.2 g of 2-(2-amino-4-thiazolyl)-2-[(Z)-[(1-piperidinecarbonyl)methoxy]imino]-acetic acid 2-benzthiazolyl thioester of melting point 146°–147° C.

(17) 99 g of ethyl 2-(2-amino-4-thiazolyl)-2-(Z)-hydroxyimino-acetate, 121.4 g of N-chloroacetylhexamethyleneimine, 238 ml of N-ethyldiisopropylamine and 103.5 g of sodium iodide are stirred at room temperature for 12 hours in 1675 ml of acetonitrile. The mixture is poured into 7 l of ethyl acetate, washed with water, dried over magnesium sulphate and concentrated. After recrystallization from isopropyl acetate, there are obtained 136 g of ethyl 2-(2-amino-4-thiazolyl)-2-[(Z)-[[(hexahydro-1H-azepin-1-yl)carbonyl]methoxy]imino]-acetate of melting point 163°-164° C.

68 g of ethyl 2-(2-amino-4-thiazolyl)-2-[(Z)-[[(hexahydro-1H-azepin-1-yl)carbonyl]methoxy]imino]-acetate are dissolved in 2.5 l of methanol and 250 ml of water and the solution is treated with 220 ml of 1N aqueous sodium hydroxide solution. The methanol is removed under reduced pressure after 48 hours. The aqueous solution is washed with ethyl acetate and treated with 220 ml of 1N aqueous hydrochloric acid. The acid which crystallizes out is filtered off and dried. There are obtained 51 g of 2-(2-amino-4-thiazolyl)-2-[(Z)-[[(hexahydro-1H-azepin-1-yl)carbonyl]methoxy]imino]-acetic acid of melting point 178°-179° C.

6.5 g of 2-(2-amino-4-thiazolyl)-2-[(Z)-[[(hexahydro-1H-azepin-1-yl)carbonyl]methoxy]imino]-acetic acid and 8 g of 2,2-dithio-bis-benzthiazole are suspended in 150 ml of acetonitrile and treated with 3.3 ml of N-methylmorpholine. 6 ml of triethyl phosphite in 40 ml of acetonitrile are added dropwise within 3 hours at 0° C. while stirring. The thioester is filtered off and dried. There are obtained 8.3 g of 2-(2-amino-4-thiazolyl)-2-[(Z)-[[(hexahydro-1H-azepin-1-yl)carbonyl]methoxy]imino]-acetic acid 2-benzthiazolyl thioester of melting point 138°-140° C.

(18) 17.7 g of ethyl 2-(2-amino-4-thiazolyl)-2-(Z)-hydroxyimino-acetate are suspended in 320 ml of acetonitrile, treated successively with 27.6 ml of N-ethyldiisopropylamine, 16 g of 5-chloromethyl-1-methyl-tetrazole and 24 g of sodium iodide and the mixture is stirred at room temperature for 12 hours. The mixture is subsequently diluted with 1.5 l of ethyl acetate, washed three times with 500 ml of water each time, dried over magnesium sulphate and concentrated. There are obtained 39.6 g of ethyl 2-(2-amino-4-thiazolyl)-2-[(Z)-[(1-methyl-1H-tetrazol-5-yl)methoxy]imino]-acetate as an oil which is used directly.

24.9 g of ethyl 2-(2-amino-4-thiazolyl)-2-[(Z)-[(1-methyl-1H-tetrazol-5-yl)methoxy]imino]-acetate are dissolved in 100 ml of methanol and the solution is treated with 250 ml of 1N aqueous sodium hydroxide solution. The mixture is stirred at room temperature for 12 hours and treated with 150 ml of water. The methanol is subsequently removed under reduced pressure. The aqueous solution is washed with ethyl acetate and treated with 250 ml of 1N aqueous hydrochloric acid. The acid crystallizes upon concentration. The acid is filtered off and, for the removal of water (about 16%), stirred for 6 hours in 350 ml of acetonitrile, filtered and dried. There are obtained 14.2 g of 2-(2-amino-4-thiazolyl)-2-[(Z)-[(1-methyl-1H-tetrazol-5-yl)methoxy]imino]-acetic acid of melting point 185° C.

5.7 g of 2-(2-amino-4-thiazolyl)-2-[(Z)-[(1-methyl-1H-tetrazol-5-yl)methoxy]imino]-acetic acid and 8 g of 2,2-dithio-bis-benzthiazole are suspended in 150 ml of acetonitrile and treated with 3.3 ml of N-methylmorpholine. The suspension is cooled to 0° C. 6 ml of triethyl phosphite in 40 ml of acetonitrile are added dropwise thereto while stirring within 2 hours. The thioester formed is filtered off and dried. There are obtained 7.7 g of 2-(2-amino-4-thiazolyl)-2-[(Z)-[(1-methyl-1H-tetrazol-5-yl)methoxy]imino]-acetic acid 2-benzthiazolyl thioester of melting point 144° C.

(19) 57.3 g of ethyl 2-(2-amino-4-thiazolyl)-2-(Z)-hydroxyimino-acetate, 80 g of N,N-diethylchloroacetamide, 138.7 ml of N-ethyldiisopropylamine and 80 g of sodium iodide are stirred at room temperature for 12 hours in 1.1 l of acetonitrile. The mixture is subsequently diluted with 5 l of ethyl acetate, washed with water, dried over magnesium sulphate and concentrated to a small volume. The compound which crystallizes out is filtered off and dried. There are obtained 68.1 g of ethyl 2-(2-amino-4-thiazolyl)-2-[(Z)-[(diethylcarbamoyl)methoxy]imino]-acetate of melting point 161° C.

68.1 g of ethyl 2-(2-amino-4-thiazolyl)-2-[(Z)-[(diethylcarbamoyl)methoxy]imino]-acetate are dissolved in 2.8 l of methanol and 240 ml of water and the solution is treated with 230 ml of 1N aqueous sodium hydroxide solution. The methanol is removed under reduced pressure after 48 hours and the aqueous solution is washed with ethyl acetate. After the addition of 230 ml of 1N aqueous hydrochloric acid, the crystallized acid is filtered off and dried. There are obtained 250.8 g of 2-(2-amino-4-thiazolyl)-2-[(Z)-[(diethylcarbamoyl)methoxy]imino]-acetic acid of melting point 180° C.

40 g of 2-(2-amino-4-thiazolyl)-2-[(Z)-[(diethylcarbamoyl)methoxy]imino]-acetic acid and 53.3 g of 2,2-dithio-bis-benzthiazole are suspended in 2 l of acetonitrile and treated with 22 ml of N-methylmorpholine. 40 ml of triethyl phosphite in 260 ml of acetonitrile are added dropwise at 0° C. within 5 hours. The crystallized thioester is filtered off and dried. There are obtained 48.8 g of 2-(2-amino-4-thiazolyl)-2-[(Z)-[(diethylcarbamoyl)methoxy]imino]-acetic acid 2-benzthiazolyl thioester of melting point 136°-137° C.

EXAMPLE 20

Manufacture of dry ampoules for intramuscular administration.

A lyophilizate of 1 g of rac,cis-3-[(Z)-2-(2-amino-4-thiazolyl)-2-[(carbamoylmethoxy)imino]acetamido]-4-methoxycarbonyl-2-oxo-1-azetidinesulphonic acid triethylamine salt is manufactured in the usual manner and filled into an ampoule. Prior to the administration, the lyophilizate is treated with 2.5 ml of a 2% aqueous lidocaine hydrochloride solution.

What is claimed is:

1. 3-[(Z)-2-(2-Amino-4-thiazolyl)-2-[(carbamoylmethoxy)imino]acetamido]-4-[(E/Z-(methoxyimino)methyl]-2-oxo-1-azetidinesulphonic acid in racemic form or in the form of the 3S-enantiomer, as well as pharmaceutically compatible salts of these compounds.

2. 3-[(Z)-2-(2-Amino-4-thiazolyl)-2-[(2-propynyloxy)iminio]acetamido]-4-carbamoyloxymethyl-2-oxo-1-azetidinesulphonic acid in racemic form or in the form of the 3S-enantiomer, as well as pharmaceutically compatible salts of these compounds.

3. 3-[(Z)-2-(2-Amino-4-thiazolyl)-2-[[2-(methylsulphonyl)ethoxy]imino]acetamido]-4-carbamoyloxymethyl-2-oxo-1-azetidinesulphonic acid in racemic form or in the form of the 3S-enantiomer, as well as pharmaceutically compatible salts of these compounds.

4. 3-[(Z)-2-(2-Amino-4-thiazolyl)-2-[(2-azidoethoxy)imino]acetamido]-4-carbamoyloxymethyl-2-oxo-1-azetidinesulphonic acid in reacemic form or in the form of the 3S-enantiomer, as well as pharmaceutically compatible salts of these compounds.

5. 3-[(Z)-2-(2-Amino-4-thiazolyl)-2-[[(1-piperidinecarbonyl)methoxy]imino]acetamido]-4-carbamoyloxymethyl-2-oxo-1-azetidinesulphonic acid in racemic form or in the form of the 3S-enantiomer, as well as pharmaceutically compatible salts of these compounds.

6. 5-[(Z)-2-(2-Amino-4-thiazolyl)-2-[[[(hexahydro-1H-azepin-1-yl)carbonyl]methoxy]imino]acetamido]-4-carbamoyloxymethyl-2-oxo-1-azetidinesulphonic acid in racemic form or in the form of the 3S-enantiomer, as well as pharmaceutically compatible salts of these compounds.

* * * * *